(12) United States Patent
Baer et al.

(10) Patent No.: US 10,751,293 B2
(45) Date of Patent: Aug. 25, 2020

(54) POLYMER FIBER SCAFFOLDS AND USES THEREOF

(71) Applicant: CASE WESTERN RESERVE UNIVERSITY, Cleveland, OH (US)

(72) Inventors: Eric Baer, Cleveland, OH (US); Gary E. Wnek, Cleveland, OH (US); Mohammad Mofidfar, Cleveland, OH (US); Jia Wang, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/757,561

(22) PCT Filed: Sep. 6, 2016

(86) PCT No.: PCT/US2016/050434
§ 371 (c)(1),
(2) Date: Mar. 5, 2018

(87) PCT Pub. No.: WO2017/041109
PCT Pub. Date: Mar. 9, 2017

(65) Prior Publication Data
US 2018/0243232 A1  Aug. 30, 2018

Related U.S. Application Data

(60) Provisional application No. 62/213,959, filed on Sep. 3, 2015.

(51) Int. Cl.
*A61K 9/70* (2006.01)
*B29C 48/08* (2019.01)
*B29C 48/21* (2019.01)
*B29C 48/00* (2019.01)
*B29C 48/18* (2019.01)
*A61L 27/54* (2006.01)
*A61L 27/48* (2006.01)
*A61K 8/02* (2006.01)
(Continued)

(52) U.S. Cl.
CPC ............ *A61K 9/7007* (2013.01); *A61K 8/027* (2013.01); *A61K 9/70* (2013.01); *A61K 31/4164* (2013.01); *A61K 47/34* (2013.01); *A61L 27/18* (2013.01); *A61L 27/26* (2013.01); *A61L 27/48* (2013.01); *A61L 27/54* (2013.01); *A61L 27/58* (2013.01); *A61Q 19/00* (2013.01); *B29C 48/023* (2019.02); *B29C 48/08* (2019.02); *B29C 48/185* (2019.02); *B29C 48/21* (2019.02); *B32B 27/08* (2013.01); *B32B 27/20* (2013.01); *B32B 27/285* (2013.01); *B32B 27/36* (2013.01); *D01D 5/08* (2013.01); *D01D 5/253* (2013.01); *D01F 1/103* (2013.01); *D01F 6/625* (2013.01); *A61K 2800/10* (2013.01); *A61K 2800/54* (2013.01); *A61L 2300/404* (2013.01); *A61L 2300/604* (2013.01); *A61L 2400/12* (2013.01); *B29K 2071/02* (2013.01); *B29K 2105/0011* (2013.01); *B29K 2105/0035* (2013.01); *B29K 2995/0062* (2013.01); *B29K 2995/0093* (2013.01); *B29L 2031/753* (2013.01); *B32B 2250/24* (2013.01); *B32B 2262/0276* (2013.01); *B32B 2307/7166* (2013.01); *B32B 2307/73* (2013.01); *D10B 2331/04* (2013.01); *D10B 2331/041* (2013.01); *D10B 2401/021* (2013.01); *D10B 2509/00* (2013.01)

(58) Field of Classification Search
CPC .......... C08L 89/00; C08L 67/04; C08L 31/04; C08L 67/02; C08L 67/06; C08L 71/02; A61L 27/26; A61L 15/26; A61L 27/48; A61L 2400/12; A61L 15/425; A61L 15/44; A61L 2300/602; A61L 2430/32; A61L 2300/404; A61L 2300/604; A61L 27/18; A61L 27/54; A61L 27/58; A61K 9/7007; A61Q 19/00; B32B 2250/24; B32B 2262/0276; B32B 2307/7166; B32B 2307/73; B32B 27/08; B32B 27/20; B32B 27/285; B32B 27/36
See application file for complete search history.

(56) References Cited

U.S. PATENT DOCUMENTS 6,461,644 B1 * 10/2002 Jackson ............... A61K 9/1635
424/499
2005/0100602 A1 * 5/2005 Sako .................... A61K 9/0004
424/468

(Continued)

FOREIGN PATENT DOCUMENTS

CN        102824641 A    * 12/2012
EP           2813212 A1  * 12/2014 ............... A61K 9/70
WO         96/00592 A2     1/1996
WO    WO-2015159305 A1  * 10/2015 ............... D01F 6/94

OTHER PUBLICATIONS

CN-102824641-A, Espacenet English Translation, downloaded Apr. 2019 (Year: 2019).*

*Primary Examiner* — Mark V Stevens
(74) *Attorney, Agent, or Firm* — Tarolli, Sundheim, Covell & Tummino LLP

(57) ABSTRACT

A multilayered polymer composite film includes a water-soluble polymer matrix and a plurality of fibers embedded within the water soluble polymer matrix. The fibers include a water insoluble polymer material and at least one of a non-polymeric hydrophobic therapeutic agent or a non-polymeric hydrophobic cosmetic agent incorporated in the water insoluble polymer material. The fibers have a rectangular cross-section, and extend the entire length of the multilayered polymer composite film.

17 Claims, 15 Drawing Sheets

(51) Int. Cl.

| | |
|---|---|
| *A61K 31/4164* | (2006.01) |
| *A61K 47/34* | (2017.01) |
| *A61L 27/18* | (2006.01) |
| *A61L 27/26* | (2006.01) |
| *A61L 27/58* | (2006.01) |
| *A61Q 19/00* | (2006.01) |
| *B32B 27/08* | (2006.01) |
| *B32B 27/20* | (2006.01) |
| *B32B 27/28* | (2006.01) |
| *B32B 27/36* | (2006.01) |
| *D01D 5/08* | (2006.01) |
| *D01D 5/253* | (2006.01) |
| *D01F 1/10* | (2006.01) |
| *D01F 6/62* | (2006.01) |
| *B29K 71/00* | (2006.01) |
| *B29K 105/00* | (2006.01) |
| *B29L 31/00* | (2006.01) |

(56) References Cited

U.S. PATENT DOCUMENTS

| | | | |
|---|---|---|---|
| 2005/0240281 A1* | 10/2005 | Slivka | A61F 2/30756 623/23.75 |
| 2006/0116755 A1 | 6/2006 | Stinson | |
| 2006/0193582 A1 | 8/2006 | Ouderkirk et al. | |
| 2010/0233458 A1* | 9/2010 | Sun | D01F 2/28 428/292.1 |
| 2014/0199364 A1 | 7/2014 | Palasis et al. | |

\* cited by examiner

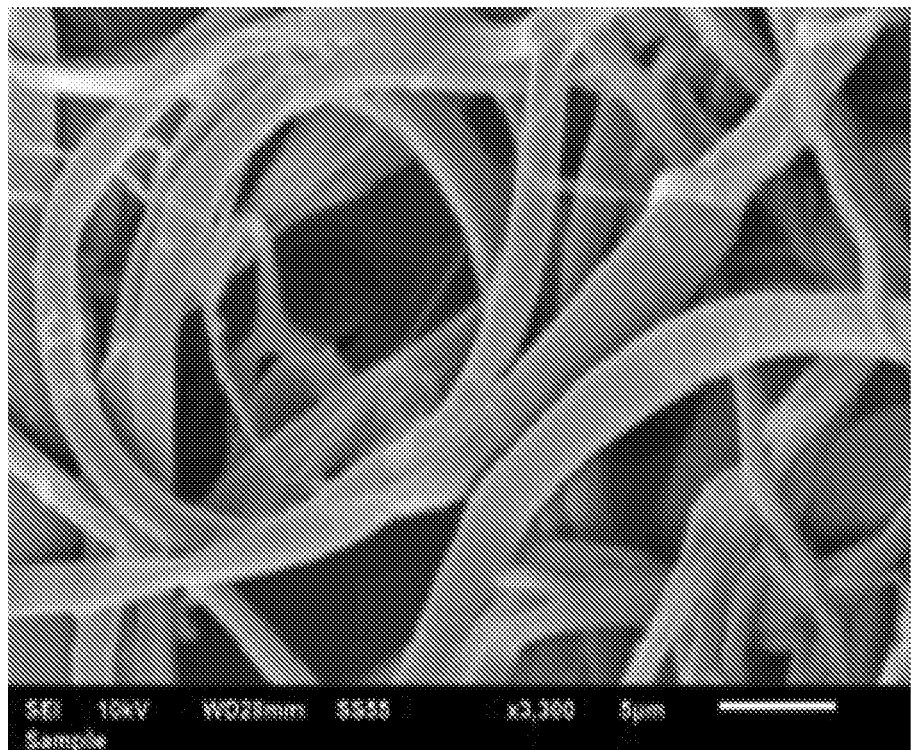
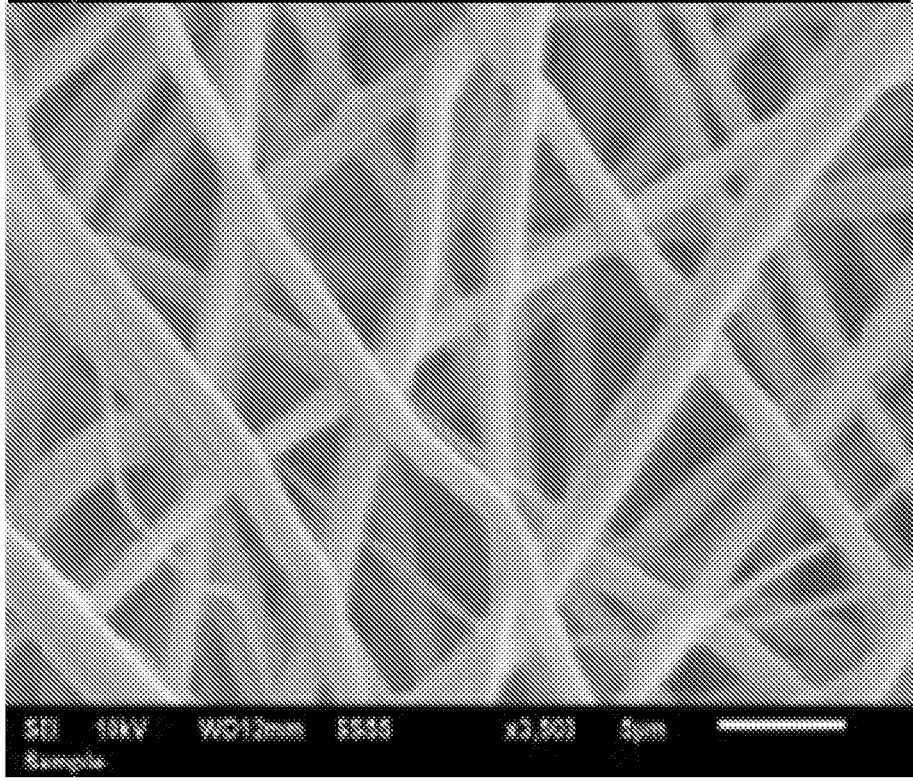
Figs. 10A-B

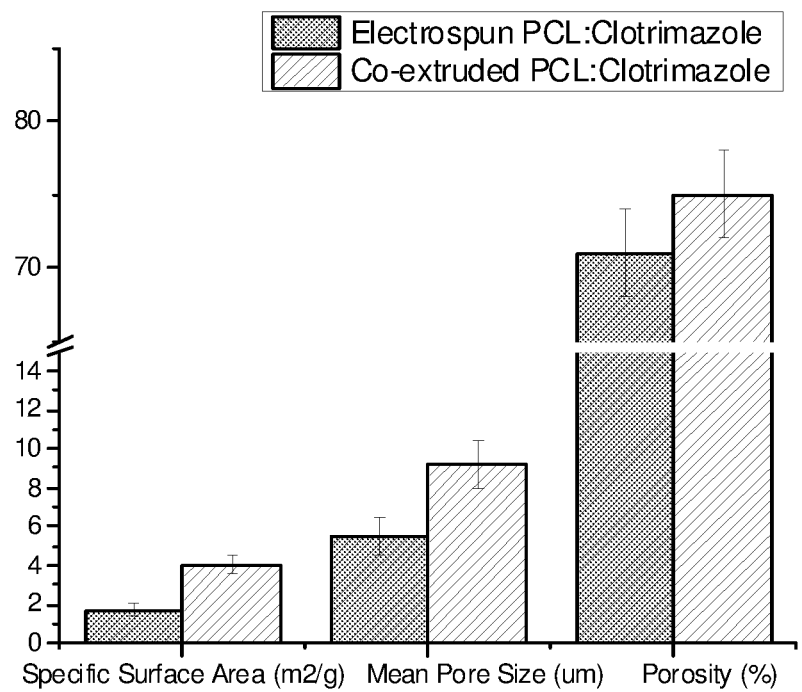
Fig. 13
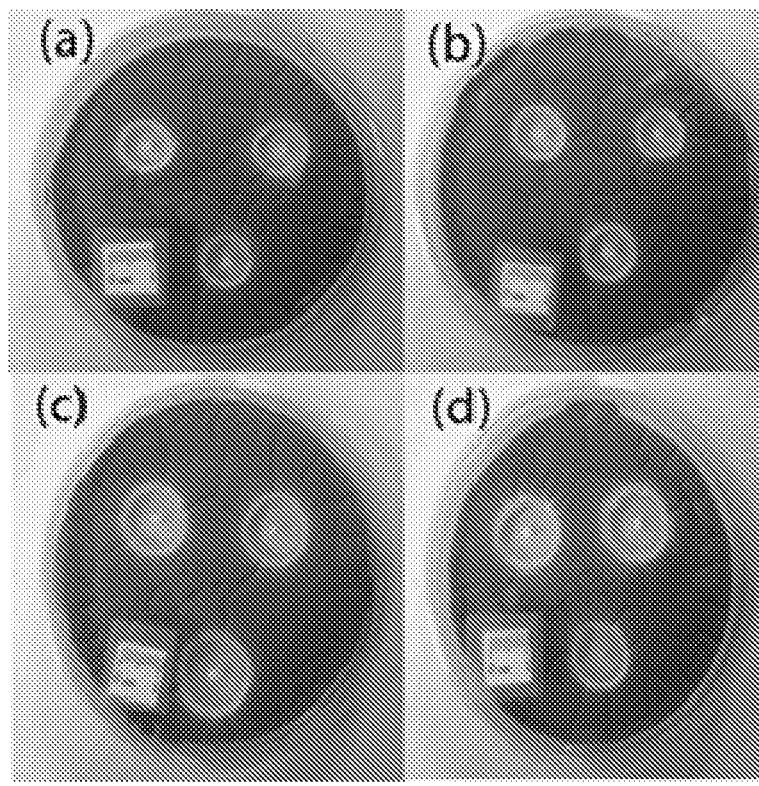
Figs. 14A-D

POLYMER FIBER SCAFFOLDS AND USES THEREOF

RELATED APPLICATION

This application claims priority from U.S. Provisional Application No. 62/213,959, filed Sep. 3, 2015, the subject matter of which is incorporated herein by reference in its entirety.

GOVERNMENT FUNDING

This invention was made with government support under Grant No. DMR0423914 awarded by The National Science Foundation. The United States government has certain rights to the invention.

BACKGROUND

Traditional industrial processes for synthetic polymer microfiber spinning can be classified as either solvent-based or melt-based. As the name implies, solvent processing involves the spinning of a polymer solution with solidification of the fiber either through coagulation in a non-solvent (wet-spinning) or solvent evaporation (dry-spinning) In contrast, melt spinning produces fibers via the spinning of molten polymer that solidifies upon cooling; drawing usually accompanies this melt-based process to induce chain orientation and enhance mechanical properties. Typically, accessing nanoscale cross-sections is difficult, where fiber diameters of only 10-20 µm are achieved with applications in the textile industry. Pushing the limits of fiber production to the nanoscale has garnered recent attention in the processing arena.

Electrospinning is perhaps the most well-known, and one of the oldest techniques for generating sub-micron fibers in lab-scale from a polymer solution, or less commonly, a polymer melt via the application of a large electric field. This charged polymer jet is subjected to electrostatic forces, which act to elongate, thin, and solidify the polymer fiber in the characteristic "whipping instability" region. Although some success has been achieved with electrospun fibers in high-value added applications, such as air filtration, topical drug delivery, and tissue engineering scaffolds, significant disadvantages are low throughput and scalability. Additionally, electrospinning necessitates large volumes of toxic solvents that must be recovered by specialized equipment to make the process viable on a large scale.

Other approaches to nanofiber fabrication have emerged, including rotary-jet spinning, gas jet blowing, melt blowing, and bicomponent fiber spinning Recent advances in rotary jet spinning have focused on a melt-based approach to nanofiber production with throughputs significantly higher than electrospinning, but improvements are ongoing to address processing complexity as it relates to broad applicability to a range of polymer systems. Melt blowing is a particularly commercially relevant and scalable technique for achieving fiber diameters on the order of tens of microns and higher; in this process, fibers are generated in-line by extrusion of a polymer through a die orifice, while a hot air jet blows down the extrudate. It is process compatible with a wide range of polymers, and is a solvent-less and environmentally-friendly manufacturing method. However, the pursuit of nanoscale fibers has been limited primarily to polypropylene for air filtration. Collectively, these limitations on nanofiber scalability increase manufacturing costs and lower productivity.

The production of continuous nanofiber has received considerable attention for drug delivery and tissue engineering applications. Incorporation of drugs and/or other biomolecules in the fiber exhibit new trend in all types of drug delivery routes, such as topical delivery, oral, intravenous, intramuscular, or inhalation usage, to reach maximum bioavailability for desired therapeutic efficacy.

Up to now, polymer fibers have been used in different applications, such as membranes, filtration, electronic sensors and reinforcing materials. Previously employed methods to produce these fibers include electrospinning of a polymer solution or melt. More specifically, the fibers were obtained by electrospinnig the polymer out of solution or the melt under high voltage. The use of this approach, however, is limited in that the proper solvents must be found and high voltage must be used, which results in high capital costs for production. Furthermore, the sizes, materials, and cross-sections of the fibers produced by electrospinning are limited. Therefore, there is a need for a process of producing polymer fibers at a reduced cost.

SUMMARY

Embodiments described herein relate to polymer fiber scaffolds, such as polymer nanofiber or microfiber scaffolds, and to their use in, for example, drug delivery applications. The polymer fiber scaffolds can be formed from a multilayered polymer composite film that includes a water-soluble polymer matrix and a plurality of fibers embedded within the water soluble polymer matrix. The fibers include a water insoluble polymer material and at least one of a non-polymeric hydrophobic therapeutic agent or a non-polymeric hydrophobic cosmetic agent incorporated in the water insoluble polymer material.

The fibers have a rectangular cross-section, and extend the entire length of the multilayered polymer composite film. The rectangular cross-section can be defined by the water soluble polymer matrix, which can be separated from the fiber to form the polymer fiber scaffold.

The height and width dimensions of the fibers can range from nanometers to micrometers to provide the fibers with a higher surface area to volume ratio than electrospun fibers having similar dimensions. For example, the fibers having a surface area to volume ratio of at least about 4 $m^2/g$. Advantageously, a multilayered polymer composite film including the fibers can be formed by a continuous solvent free process and a polymer fiber film form from the film can provide controlled delivery, higher output, and higher release of hydrophobic drug compared to electrospun fibers.

In some embodiments, the water soluble polymer can be coextruded with the water insoluble polymer material and the at least one of a non-polymeric hydrophobic therapeutic agent or a non-polymeric hydrophobic cosmetic agent. The water insoluble polymer material can substantially immiscible with the water soluble polymer during coextrusion to allow formation of distinct fibers having rectangular cross-section. For example, the water soluble polymeric matrix comprises polyethylene oxide and the water insoluble polymer material comprises polycaprolactone.

In other embodiments, the hydrophobic therapeutic agent is at least partially soluble in the water insoluble polymer material. The fibers can include about 1% to about 50% by weight of the non-polymeric hydrophobic therapeutic agent or the non-polymeric hydrophobic cosmetic agent. In some embodiments, the non-polymeric hydrophobic therapeutic agent is clotrimazole that is incorporated in the fibers at about 1% to about 20% by weight.

Other embodiments relate to a method of producing polymer fiber scaffold that can be used to deliver at least one of a non-polymeric hydrophobic therapeutic agent or a non-polymeric hydrophobic cosmetic agent to a subject in need thereof. The method can include extruding a water soluble polymer material to form a first layer and a water insoluble polymer material and at least one of a non-polymeric hydrophobic therapeutic agent or a non-polymeric hydrophobic cosmetic agent to form a second layer. The first layer can layered over the second layer. The overlapping layers can be multiplied to form a multilayered composite film that includes a water soluble polymer matrix and a plurality of fibers embedded within the water soluble polymer matrix. The water soluble polymer matrix can then be separated from the fibers water insoluble polymer material to form a polymer fiber scaffold that includes a plurality of fibers having a rectangular cross-section.

In some embodiments, the water soluble polymer can be coextruded with the water insoluble polymer material and the least one of a non-polymeric hydrophobic therapeutic agent or a non-polymeric hydrophobic cosmetic agent. The water insoluble polymer material can be substantially immiscible with the water soluble polymer during coextrusion. The first layer can include about 90% by weight of the overlapping layers and the second layer can include about 10% by weight of the overlapping layers.

In some embodiments, multiplying the overlapping layers comprises vertical layer multiplication of the overlapping first layer and second layer by cutting the flow horizontally of the overlapping layers through a die, surface layering the water soluble polymer material on a top and bottom surface of vertical layers formed by the vertical layer multiplication, and horizontal layer multiplication of the surface layered vertical layers to stack one side portion of the surface layered vertical stack on a second side portion. In some embodiments, the vertical layer multiplication is repeated eight times to yield vertical layers composed of 1024 alternating 512 layers of the first layer and 512 layers of second layer. The processing temperature used to form the multilayered polymer composite film can be about 180° C.

In other embodiments, separating the water soluble polymer matrix from the fibers of water insoluble polymer material and at least one of a non-polymeric hydrophobic therapeutic agent or a non-polymeric hydrophobic cosmetic agent can include, for example, subjecting the multilayered composite film to a high pressure water stream or a high pressure air stream, or dissolving the second polymer material. For example, the water soluble polymer matrix can be separated from the fibers of water insoluble polymer material and at least one of a non-polymeric hydrophobic therapeutic agent or a non-polymeric hydrophobic cosmetic agent by immersing the multilayered composite film in a water to dissolve the water soluble polymer material of the matrix.

BRIEF DESCRIPTION OF THE DRAWINGS

FIG. 10 illustrates SEM images of a) co-extruded and b) electrospun PCL:Clotrimazole fibers with 4% drug loading.

FIG. 13 illustrates a graph showing surface area, porosity, and mean pore size for electrospun and co-extruded fibers.

DETAILED DESCRIPTION

Embodiments described herein relate to polymer fiber (nanofiber or microfiber) scaffolds, methods of forming the polymer fiber scaffolds, and to the use of the scaffolds in, for example, drug delivery and/or wound healing applications. The polymer fiber scaffolds can include a plurality of non-woven or woven fibers that are formed from commodity polymers using a continuous extrusion process.

The polymer fibers or polymer fiber scaffold of the fibers can be formed from a multilayered polymer composite film that includes a water-soluble polymer matrix and a plurality of fibers embedded within the water soluble polymer matrix. The fibers include a water insoluble polymer material and at least one of a non-polymeric hydrophobic therapeutic agent or a non-polymeric hydrophobic cosmetic agent incorporated in the water insoluble polymer material.

The fibers have a rectangular cross-section, and extend the entire length of the multilayered polymer composite film. The rectangular cross-section is defined by the water soluble polymer matrix, which can be separated from the fiber to form the polymer fibers and scaffold there from.

The height and width dimensions of the fibers can range from nanometers to micrometers. For example, the fibers can have a rectangular cross-section of about 10 nm (height)×10 nm (width) to about 100 μm×100 μm, with variations in between.

Advantageously, the polymer scaffold can be formed or fabricated using solely commercially available polymers water soluble polymer and water insoluble polymers, such as poly(ethylene oxide) (PEO) and PCL. The process used to form the polymer fiber scaffold can be solvent-free, allow for controllable cross-sectional dimensions of the fibers, and use FDA-friendly polymers during processing. The fabrication process is flexible because it involves the use of an extrusion line that is composed of several basic multipliers. Arrangement of these multipliers allows control over the number, as well as the dimensions, of fibers contained in one extrudate. In addition, the cross-sectional geometry of the nanofibers is rectangular creating greater surface area to volume ratios (e.g., at least about 2 $m^2$/mg, at least about 4 $m^2$/mg or more), when compared to cylindrical fibers formed by, for example electrospinning. The increased surface area can provide controlled delivery, higher output, and higher release relates of the at least one of a non-polymeric hydrophobic therapeutic agent or a non-polymeric hydrophobic cosmetic agent compared to electrospun fibers having similar dimension.

Figure 1:
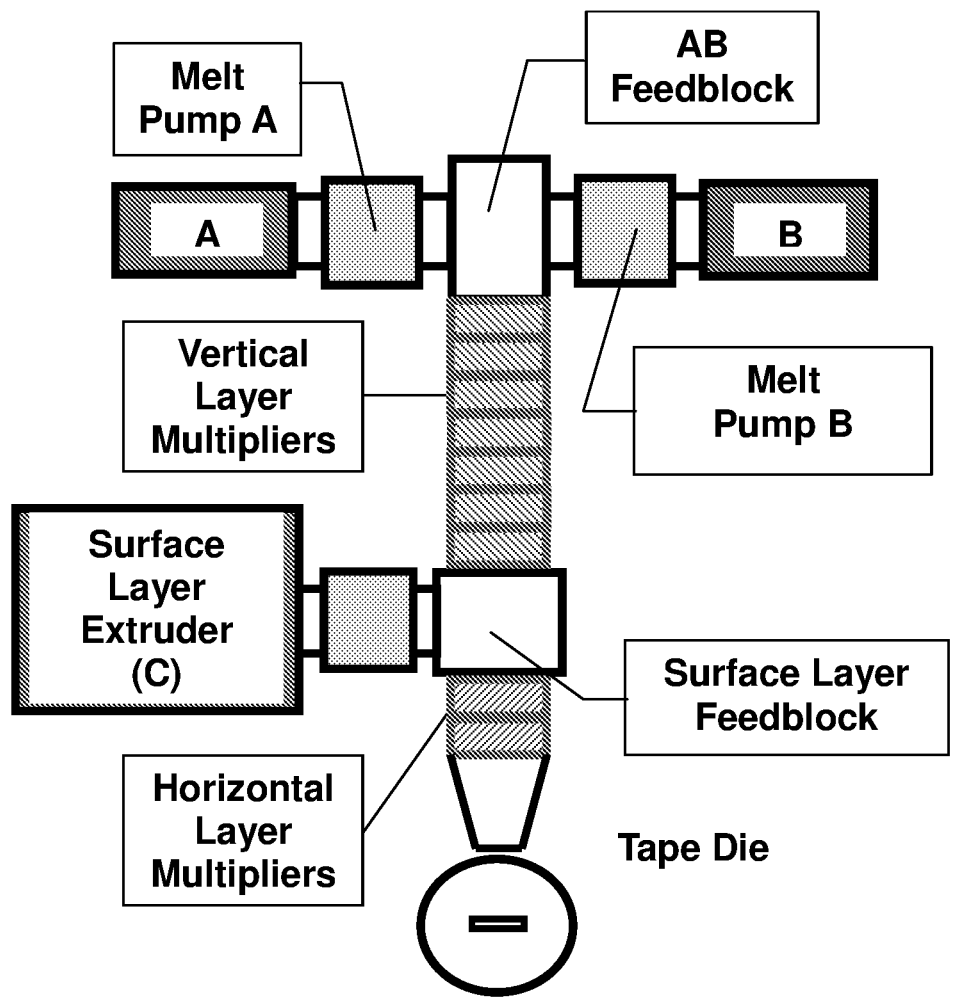
FIG. 1 is a schematic illustration of a co-extrusion and vertical multiplication process in accordance with an embodiment.

In some embodiments, as illustrated in FIG. 1, the water soluble polymer can be coextruded with the water insoluble polymer material and the at least one of a non-polymeric hydrophobic therapeutic agent or a non-polymeric hydrophobic cosmetic agent to form an overlapping first layer and second layer. The water insoluble polymer material can be substantially immiscible with the water soluble polymer during coextrusion to allow formation of distinct fibers having rectangular cross-section. For example, the water soluble polymeric matrix comprises polyethylene oxide and the water insoluble polymer material comprises polycaprolactone.

The overlapping layers can be multiplied to form a multilayered composite film that includes a water soluble polymer matrix and a plurality of fibers embedded within the water soluble polymer matrix. The water soluble polymer matrix can then be separated from the fibers water insoluble polymer material to form a polymer fiber scaffold that includes a plurality of fibers having a rectangular cross-section.

In some embodiments, the water soluble polymer can be coextruded with the water insoluble polymer material and the least one of a non-polymeric hydrophobic therapeutic agent or a non-polymeric hydrophobic cosmetic agent. The water insoluble polymer material can be substantially immiscible with the water soluble polymer during coextrusion. The first layer can include about 90% by weight of the overlapping layers and the second layer can include about 10% by weight of the overlapping layers.

Figure 2:
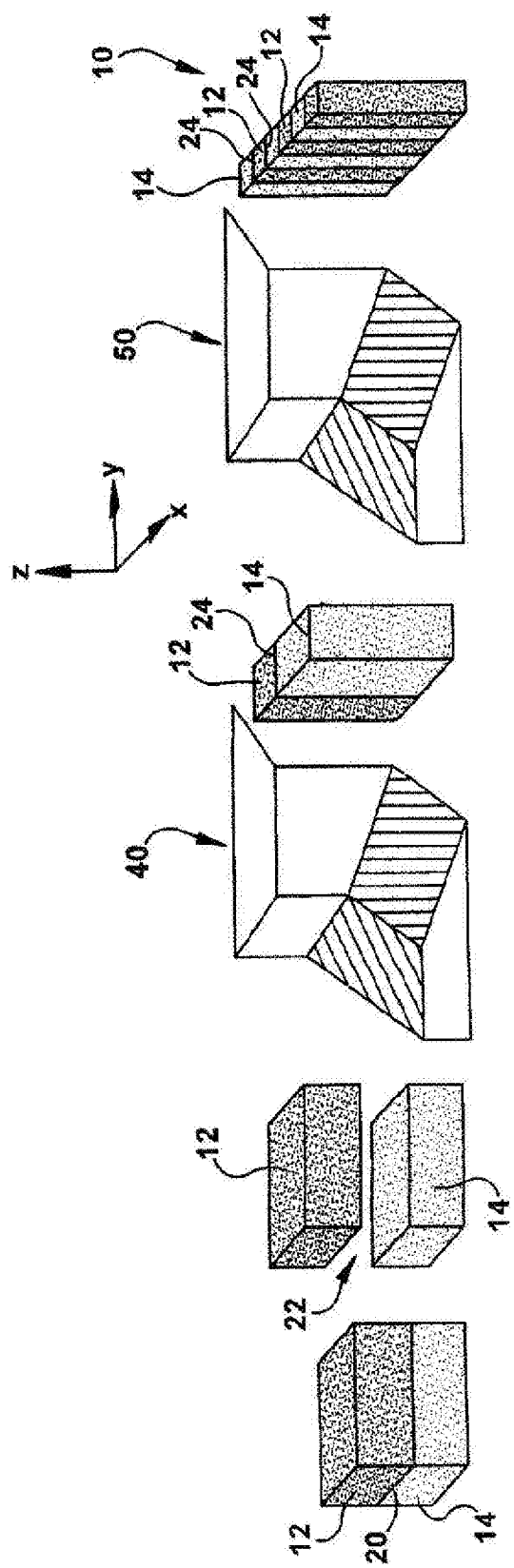
FIG. 2 is a schematic illustration of a coextrusion and layer multiplying process used to form a multilayered polymer composite film in accordance with an embodiment.

In some embodiments, multiplying the overlapping layers comprises vertical layer multiplication of the overlapping first layer and second layer by cutting the flow horizontally of the overlapping layers through a die, surface layering the water soluble polymer material on a top and bottom surface of vertical layers formed by the vertical layer multiplication, and horizontal layer multiplication of the surface layered vertical layers to stack one side portion of the surface layered vertical stack on a second side portion. In some embodiments, the vertical layer multiplication is repeated eight times to yield vertical layers composed of 1024 alternating 512 layers of the first layer and 512 layers of second layer FIG. 2 illustrates a coextrusion and multiplying process used to form a multilayered polymer composite film 10. First, a first polymer layer 12 and a second polymer layer 14 are provided. The first layer 12 is formed from a water soluble polymeric material (a) and the second polymer layer 14 is formed from a water insoluble polymer material (b) and at least one of a non-polymeric hydrophobic therapeutic agent or a non-polymeric hydrophobic cosmetic agent incorporated in the water insoluble polymer material. The water insoluble polymer material can be substantially immiscible and have a similar viscosity with the water soluble polymer material (a) when coextruded. It will be appreciated that one or more additional layers formed from the polymer materials (a) or (b) or a different polymer materials may be provided to produce the multilayered polymer composite film 10.

The term "polymer", "polymer material", or "polymeric material" as used in the present application denotes a material having a weight average molecular weight (Mw) of at least 5,000. Preferably the polymer is an organic polymeric material. The term "oligomer" or "oligomeric material" as used in the present application denotes a material with a weight average molecular weight of from 1,000 to less than 5,000. Such polymeric materials can be glassy, crystalline or elastomeric polymeric materials.

Examples of water soluble polymer materials that can potentially be used include, but are not limited to, polyethylene oxide, polyethylene glycol, polyvinyl alcohol, polyethylene imines (PEI), polyacrylamide (PAM), polyamide amines, polyamine based polymers, polyvinyl alcohol and copolymers thereof, poly(acrylic acid), polymethacrylate, other acrylic polymers, poly(vinyl pyrrolidone) (PVP), polyethers, and water soluble natural polymers, such as cellulose and cellulose derivatives. In one embodiment, the water soluble polymer can include polyethylene oxide.

Examples of water insoluble polymers are non-polar polymers, such as polycaprolactone (PCL), polyethylene terephthalates, polyethylene naphthalates, polypropylene, polyethylene, and polytetrafluoroethylene. Additional polymeric materials include block or graft copolymers. In one instance, the polymeric materials used to form the layers 12, 14 may constitute thermoplastics that are substantially immiscible during coextrusion. In addition, each individual layer 12, 14 may include blends of two or more water soluble polymers or copolymers and water insoluble polymers or copolymers, preferably the components of the blend are substantially miscible with one another yet still maintaining substantial immiscibility between the layers 12, 14. The components comprising the layers 12, 14 can include organic or inorganic materials, including nanoparticulate materials, designed, for example, to modify the mechanical properties of the components, e.g., tensile strength. It will be appreciated that potentially any extrudable water soluble polymer can be used as the water soluble polymer material (a) and any extrudable water insoluble polymer can be used as the water insoluble polymer material (b) so long as upon coextrusion such polymer materials (a), (b) are substantially immiscible and form discrete layers or polymer regions. Such materials can have a substantially similar viscosity upon coextrusion.

In some embodiments, the polymers used for the water soluble polymer and the water insoluble polymer can be biodegradable and/or substantially biocompatible or cytocompatible (i.e., substantially non-cytotoxic). The use of biodegradable and substantially biocompatible or cytocompatible polymers allows polymer fiber scaffold to be formed that can be used in medical applications, such as therapeutic agent delivery and wound healing. Examples of that polymers that are substantially biocompatible or cytocompatible include water insoluble polymer, PCL, paired with water soluble polymer, PEO.

The at least one of a non-polymeric hydrophobic therapeutic agent or a non-polymeric hydrophobic cosmetic agent incorporated in the water insoluble polymer material can be selected from any hydrophobic therapeutic agent or cosmetic agent that is at least partially soluble in or has a substantially similar solubility parameter as the water insoluble polymer. In some embodiments, the hydrophobic therapeutic agent or cosmetic agent can have a Hansen solubility parameter that allows the hydrophobic therapeutic agent or cosmetic agent to be readily incorporated in the water insoluble polymer material of the fibers and readily diffuse from the fibers to tissue, such as skin, when the polymer fiber scaffold is applied to the tissue.

For example, a consideration of Hansen solubility parameters suggests the PCL is a good match for clotrimazole.

TABLE 1

Hansen Solubility Parameters

|  | $\delta_D$ | $\delta_P$ | $\delta_H$ |
|---|---|---|---|
| Skin | 17.12 | 3.03 | 13.89 |
| PCL | 17.70 | 5.00 | 8.40 |
| Clotrimazole | 20.80 | 3.60 | 1.60 |

In some embodiments, the hydrophobic therapeutic agent can include, for example, analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole; anti-arrhythmic agents: amiodarone HCl, disopyramide, flecamide acetate, quinidine sulphate: anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants: dicoumarol, dipyridamole, nicoumalone, phenindione; anti-depressants: amoxapine, maprotiline HCl, mianserin HCL, nortriptyline HCl, trazodone HCL, trimipramine maleate; anti-diabetics: acetohexamide, chlorpropamide, glibenclamide, gliclazide, glipizide, tolazamide, tolbutamide, anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid; anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid; anti-gout agents: allopurinol, probenecid, sulphin-pyrazone; anti-hypertensive agents: amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-malarials: amodiaquine, chloroquine, chlorproguanil HCl, halofantrine HCl, mefloquine HCl, proguanil HCl, pyrimethamine, quinine sulphate; anti-migraine agents: dihydroergotamine mesylate, ergotamine tartrate, methysergide maleate, pizotifen maleate, sumatriptan succinate; anti-muscarinic agents: atropine, benzhexyl HCl, biperiden, ethopropazine HCl, hyoscyamine, mepenzolate bromide, oxyphencyclimine HCl, tropicamide; anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole; anti-thyroid agents: carbimazole, propylthiouracil; anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone; beta-blockers, acebutolol, alprenolol, atenolol, labetalol, metoprolol, nadolol, oxprenolol, pindolol, propranolol; cardiac inotropic agents: amrinone, digitoxin, digoxin, enoximone, lanatoside C, medigoxin; corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; diuretics: acetazolamide, amiloride, bendrofluazide, bumetanide, chlorothiazide, chlorthalidone, ethacrynic acid, frusemide, metolazone, spironolactone, triamterene; anti-parkinsonian agents: bromocriptine mesylate, lysuride maleate; gastro-intestinal agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine; histamine H; receptor antagonists: acrivastine, astemizole, cinnarizine, cyclizine, cyproheptadine HCl, dimenhydrinate, flunarizine HCl, loratadine, meclozine HCl, oxatomide, terfenadine; lipid regulating agents: bezafibrate, clofibrate, fenofibrate, gemfibrozil, probucol; nitrates and other anti-anginal agents: amyl nitrate, glyceryl trinitrate, isosorbide dinitrate, isosorbide mononitrate, pentaerythritol tetranitrate; nutritional agents: betacarotene, vitamin A, vitamin B2, vitamin D, vitamin E, vitamin K; opioid analgesics: codeine, dextropropyoxyphene, diamorphine, dihydrocodeine, meptazinol, methadone, morphine, nalbuphine, pentazocine; sex hormones; clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone; stimulants: amphetamine, dexamphetamine, dexfenfluramine, fenfluramine, mazindol; and mixtures of hydrophobic drugs may, of course, be used where therapeutically effective.

The hydrophobic cosmetic agent can include, for example, fragrances, examples of which are dihydromyrcenol, limonene, benzyl acetate, Romascone; antibacterial agents, examples of which are chlorhexidine, triclosan; and for skin therapy, examples are some cosmetic applications also use vitamins and nutraceuticals.

In some embodiments, the non-polymeric hydrophobic therapeutic agent or a non-polymeric hydrophobic cosmetic agent can be provided in the water insoluble polymer material at about 1% to about 50% by weight, for example, about 1% to about 20%, by weight.

Referring to FIG. 2, the layers 12, 14 are co-extruded and multiplied in order to form the multilayered polymer composite film 10. In particular, a pair of dies 40, 50 is used to coextrude and multiply the layers 12, 14. Each layer 12, 14 initially extends in the y-direction of an x-y-z coordinate system. The y-direction defines the length of the layers 12, 14 and extends in the general direction of flow of material through the dies 40, 50. The x-direction extends transverse, e.g., perpendicular, to the y-direction and defines the width of the layers 12, 14. The z-direction extends transverse, e.g., perpendicular, to both the x-direction and the y-direction and defines the height or thickness of the layers 12, 14.

The layers 12, 14 are initially stacked in the z-direction and define an interface 20 therebetween that resides in the x-y plane. As the layers 12, 14 approach the first die 40 they are separated from one another along the z-axis to define a space 22 therebetween. The layers 12, 14 are then re-oriented as they pass through the first die 40. More specifically, the first die 40 varies the aspect ratio of each layer 12, 14 such that the layers 12, 14 extend longitudinally in the z-direction. The layers 12, 14 are also brought closer to one another until they engage or abut one another along an interface 24 that resides in the y-z plane. .

The layers 12, 14 then enter the second die 50 where layer multiplication occurs. The second die 50 may constitute a single die or several dies which process the layers 12, 14 in succession (not shown). Each layer 12, 14 is multiplied in the second die 50 to produce a plurality of first layers 12 and a plurality of second layers 14 that alternate with one another to form the multilayered polymer composite film 10. Each pair of layers 12, 14 includes the interface 24 that resides in the y-z plane. The layers 12, 14 are connected to one another generally along the x-axis to form a series of discrete, alternating layers 12, 14 of polymer material (a), (b). Although three of each layer 12 and 14 are illustrated it will be appreciated that the multilayered polymer composite film 10 may include, for example, up to thousands of each layer 12, 14.

Figure 4:
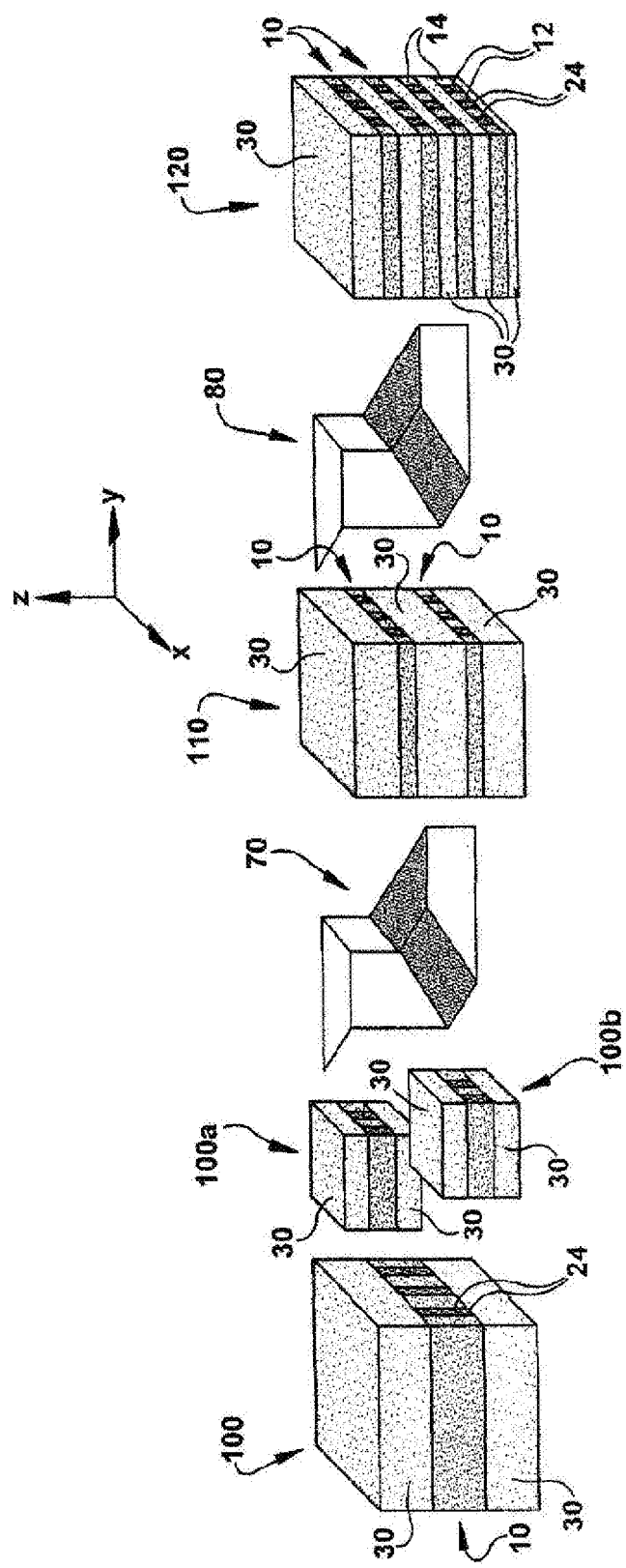
FIG. 4 is a schematic illustration of additional layer multiplying steps for the composite stream of FIG. 2.

Referring to FIG. 4, once the multilayered polymer composite film 10 is formed a detachable skin or surface layer 30 is applied to the top and bottom of the film 10 such that the film 10. In particular, the multilayered polymer composite film 10 enters a die 60 where the film 10 is sandwiched between two skin layers 30 along the z-axis to form a first composite stream 100. The skin layer 30 may be formed from the water soluble polymer material (a), or a polymer material (c) different from the water soluble polymer material (a) and water insoluble polymer material ((b). One or both of the skin layers 30 may, however, be omitted (not shown).

Referring to FIG. 4, the first composite stream 100 is divided along the x-axis into a plurality of branch streams 100a, 100b and processed through a pair of multiplying dies 70, 80. In the die 70, the streams 100a, 100b are stacked in the z-direction, stretched in both the x-direction and the y-direction, and recombined to form a second composite stream 110 that includes a plurality of multilayered films 10 alternating with skin layers 30. Biaxial stretching of the branch streams 100a, 100b in the x-direction and y-direction may be symmetric or asymmetric.

Figure 3:
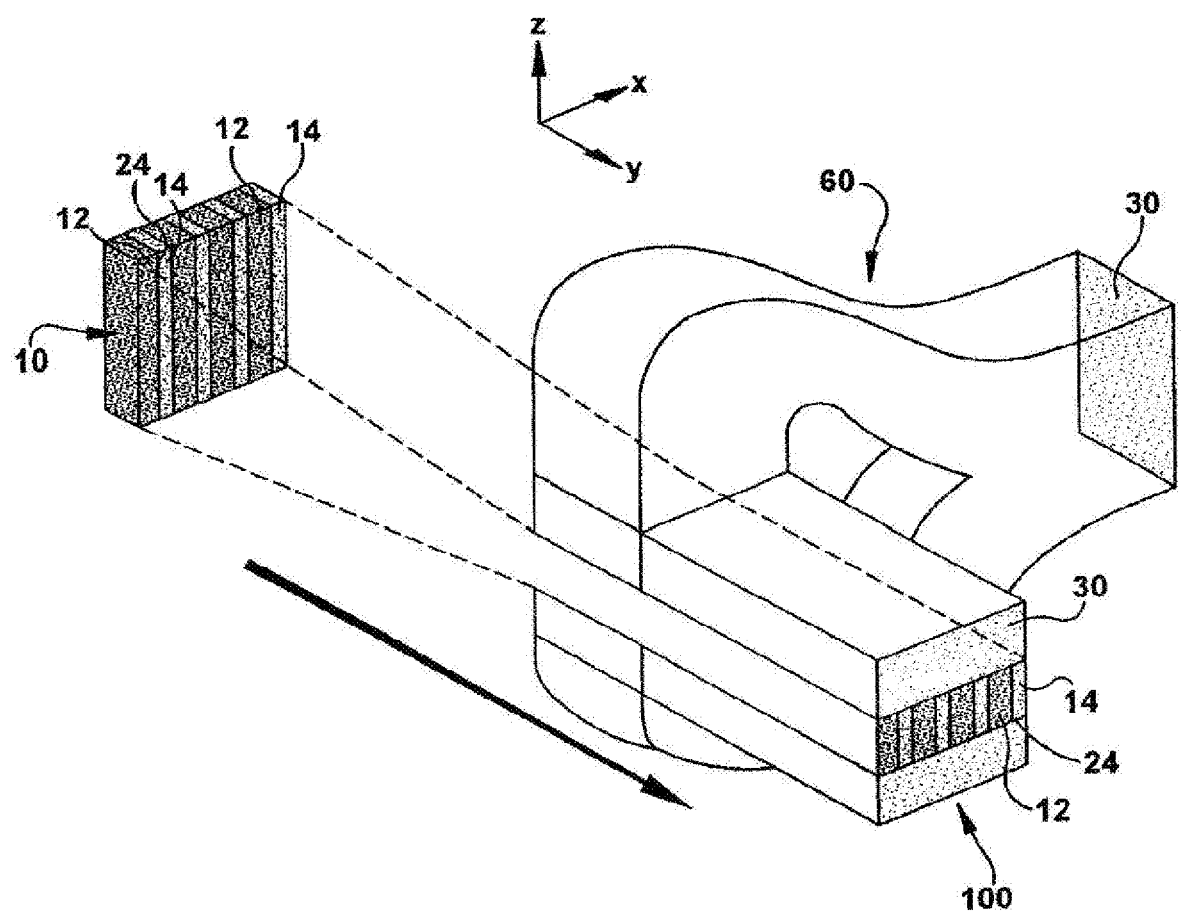
FIG. 3 is a schematic illustration of coextruding skin layers onto the composite film of FIG. 1 to form a composite stream.

The die 80 performs similar modifications to the second composite stream 110 that the die 70 performed on the branch streams 100a, 100b. In particular, in the die 80 the second composite stream 110 is divided along the x-axis, stacked along the z-axis, stretched in both the x-direction and the y-direction, and stacked in the z-direction to form a third composite stream 120. The third composite stream 120 shown in FIG. 3 includes four multilayered composite films 10 that alternate with five skin layers 30, although more or fewer of the films 10 and/or layers 30 may be present in the third composite stream 120. Regardless, the third composite stream 120 includes a plurality of layer interfaces 24 between the layers 12, 14.

By changing the volumetric flow rate of the polymer layers 12, 14 through the dies 70, 80, the thickness of both the polymer layers 12, 14 and each multilayered polymer film 10 in the z-direction can be precisely controlled. Additionally, by using detachable skin layers 30 and multiplying the composite streams 100, 110 within the dies 70, 80, the number and dimensions of the layers 12, 14, the multilayered polymer film 10, and the branch streams 100a, 100b in the x, y, and z-directions can be controlled.

Figure 5A:
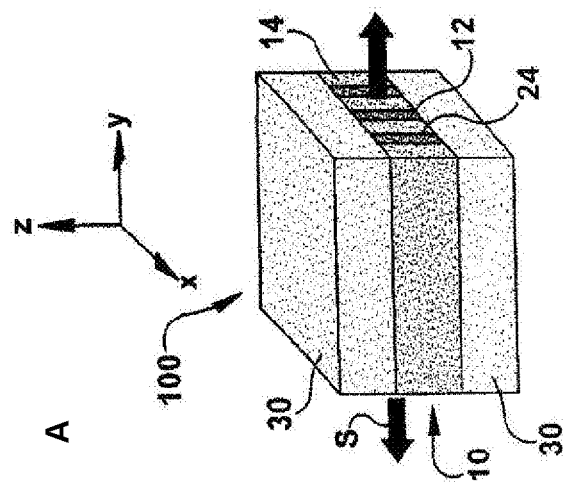
FIG. 5A is a schematic illustration of stretching the composite stream of FIG. 2.
Figure 5B:
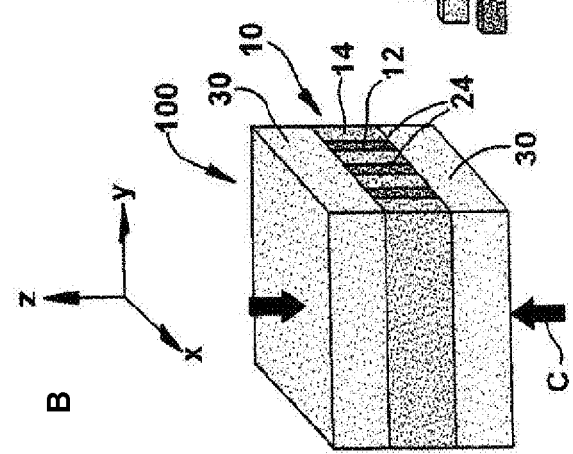
FIG. 5B is a schematic illustration of compressing the composite stream of FIG. 2.

Referring to FIGS. 5A and 5B, the first composite structure 100 may be mechanically processed by, for example, at least one of orientation (FIG. 4A), compression (FIG. 4B), and ball-mill grinding (not shown). As shown, the composite stream 100 is stretched in the y-direction as indicated generally by the arrow "S", although the composite stream 100 may alternatively be stretched in the x-direction (not shown). FIG. 5B illustrates the composite stream 100 being compressed in the z-direction as indicated generally by the arrow "C". The degree of stretching and/or compression will depend on the application in which the nanofibers and/or scaffold formed from the multilayered polymer film 10 is to be used. The ratio of y-directional stretching to z-direction compression may be inversely proportional or disproportional.

In one embodiment, the multilayer film can be uniaxially stretched in the y-direction or S-direction at a draw ratio of about 1 to about 10 to decrease the cross-sectional dimension of the fibers and increase the surface area of the nanofibers and scaffold so formed.

Figure 5C:
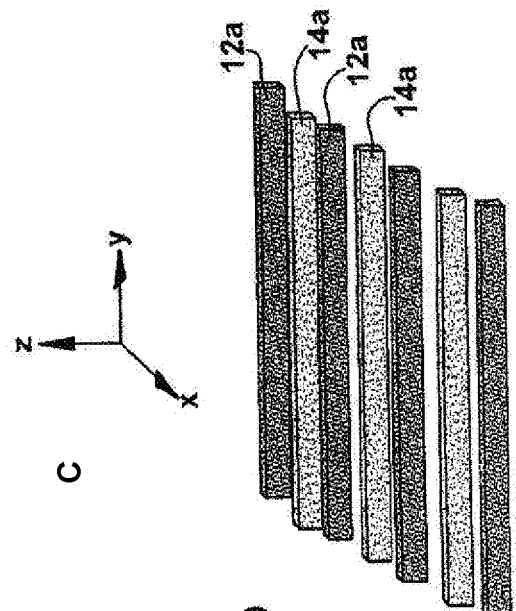
FIG. 5C is a schematic illustration of delaminating the composite stream of FIG. 2.

Referring to FIG. 5C, the first composite stream 100 can be further processed to cause the components 12, 14, 30 thereof to separate or delaminate from one another and form a plurality of fibers or fiber-like structures 12a or 14a from the layers 12, 14. The removed skin layers 30 are discarded.

Alternatively, the water soluble polymer material (a) of the layer 12 be dissolved in water remove the water soluble polymer matrix and provide a polymer fiber scaffold. Accordingly, immersing the composite stream 100 in the water separates the layers 12, 14 by wholly removing, e.g., dissolving, not only the interfaces 24 between the layers 12, 14 but removed the soluble layers 12 entirely. The insoluble layers 14 are therefore left behind following water immersion. The same solvent or a different solvent may be used to dissolve the skin layers 30, when present. The remaining soluble layers 14 form the fibers 14a. In one instance, the solvent can be water and in some instances no organic solvent is used. In one example, a composite film as described herein comprising a PEO matrix and PCL fibers including the hydrophobic therapeutic agent or cosmetic agent can be immersed in water for up to 3 days to remove the PEO matrix and form the fibers.

Figure 6:
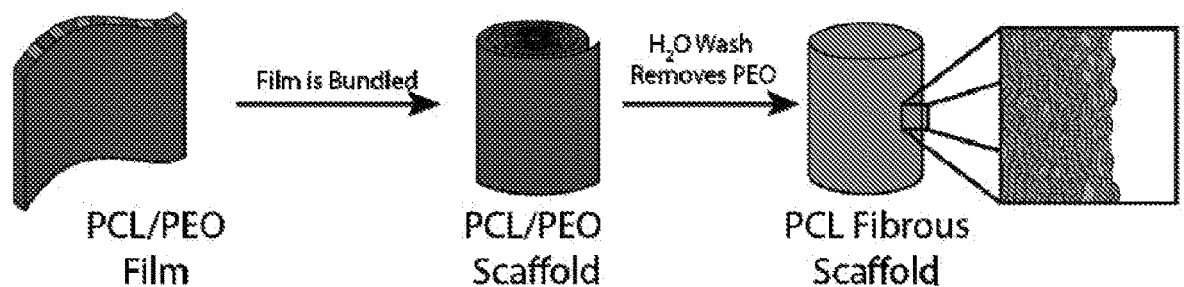
FIG. 6 is a schematic illustration of delaminating a composite stream to form a scaffold.

Optionally, as illustrated in FIG. 6, a multilayer composite stream that includes a polymer material soluble in a particular solvent and another polymer material insoluble in that solvent can be bundled or consolidated prior to solvent immersion Immersing the bundled composite stream in the solvent separates the layers and forms a scaffold of the polymer fibers.

In another instance, the layers 12, 14, 30 are mechanically separated by high pressure water jets (not shown). In particular, two opposing ends of the composite stream 100 can be fixed and water jets with a nozzle pressure of no less than about 2000psi can be applied to the composite stream 100 to separate the layers 12, 14, 30 completely, thereby forming the nano-fibers 12a, 14a. More specifically, applying high pressure water to the first composite stream 100 removes the interfaces 24 between the layers 12, 14, i.e., delaminates the multilayered polymer composite films 10, to form the fibers 12a and 14a. Although delamination of the first composite stream 100 is illustrated, it will be appreciated that the multilayered polymer composite film 10, the second composite stream 110 or the third composite stream 120 may likewise be delaminated via high pressure water or the like to form the fibers 12a, 14a.

Whether the fibers are formed by mechanically separating the layers or dissolving the water insoluble layer with water, the fibers produced by the described coextrusion process have rectangular cross-sections rather than the conventional, round cross-sections formed by electrospinning These rectangular or ribbon-like fibers have a larger surface area-to-volume ratio than round fibers developed using spinning methods. Regardless of the method of separation enlisted, the fibers can stretch, oscillate, and separate from each other at the interface. Furthermore, due to the aforementioned mechanical processing techniques of FIGS. 5A and 5B, the exact cross-sectional dimensions of the rectangular fibers can be precisely controlled. For example, the rectangular fibers can be made smaller and strengthened via mechanical processing.

Due to the construction of the first composite stream 100 and the fixed sizes of the dies 40-80, the composition of the vertical layers 12, 14 and surface layers 30 is proportional to the ratio of the height in the z-direction of a vertical layer 12, 14 section to that of a surface layer 30 section. Therefore, if the layer 12 (or 14) is selected to form the rectangular fibers 12a (or 14a), the thickness and height of the final fibers 12a (or 14a) can be adjusted by changing the ratio of the amount of the layers 12, 14 as well as the amount of surface layer 30. For example, increasing the percentage of the amount of the material (b) of the layers 14 relative to the amount of the material (a) of the layers 12 and/or increasing the amount of the material of the surface layers 30 results in smaller rectangular fibers 12a. Alternatively, one or more of the dies 40-80 may be altered to produce nanofibers 12, 12a, 14, 14a having a size and rectangular cross-section commensurate with the desired application. In one instance, one or more of the dies 40-80 could be modified to have a slit or square die construction to embed the fibers 12, 12a, 14, 14a within the surface layers 30.

The extrusion process can be tailored to produce vertically layered films 10 with designer layer/fiber thickness distributions. For example, the relative material compositions of the polymers (a), (b) of the layers 12, 14 can be varied with great flexibility to produce rectangular polymer fibers 12, 12a, 14, 14a with highly variable constructions, e.g., 50/50, 30/80, 80/30, etc. The rectangular polymer fibers 12, 12a, 14, 14a can be highly oriented and strengthened by post-extrusion orienting. Furthermore, a wide magnitude of layer 12, 14 thicknesses in the z-direction is achievable from a few microns down to tens of nanometers depending on the particular application.

The polymer fibers so formed can be consolidated to produce polymer nanofiber scaffolds. In one embodiment, as shown in FIG. 6, the fibers can be consolidated by bundling the composite stream prior to separation of the fibers or salvation of a polymer. In other embodiments, the fibers can be consolidated by compressing, weaving, and physically mixing the fibers.

The fiber scaffolds can have various densities and porosities depending on the fiber cross-section and the process used to consolidate the fibers. For example, the scaffolds can have a porosity of about 1% by volume to about 90% by volume, and a pore size of about 1 μm to about 100 μm. In some embodiments, each fiber can have a rectangular cross section of 10 nm (height)×10 nm (width) to about 10 μm×10 μm, with variations in between. The nanofibers can have surface area of at least about 1 $m^2$/mg, at least about 2 $m^2$/mg, at least about 4 $m^2$/mg or more.

In some embodiments, the polymer fiber scaffolds can be used in a variety of biomedical applications, including drug delivery, wound healing, and regenerative medicine applications. Advantageous, such scaffolds can have high surface area (e.g., greater than about 2 $m^2$/mg of fiber) and high aspect ratio fibers for promoting cell adherence, growth, proliferation, and differentiation. The polymer fiber scaffolds can also facilitate liquid and gas transport (e.g., facilitate oxygenation of tissue and efflux of waste products from the tissue) as well as controlled delivery, higher output, and higher release rates of the at least one non-polymeric hydrophobic therapeutic agent or non-polymeric hydrophobic cosmetic agent.

In one example, the polymer fiber scaffold can be used as a substrate for a wound dressing. The wound dressing can have a length, a width, and a thickness that may be varied depending upon the particular application. For example, the wound healing dressing can have a sleeve-like or cylindrical configuration as well as a rectangular or square-shaped configuration. In one example, the wound healing dressing can have a thickness of about 1 cm to about 10 cm or greater, a length of about 2 cm to about 30 cm or greater, and a width of about 2 cm to about 30 cm or greater.

In some embodiments, the wound dressing can include a hydrophobic anti-fungal agent or anti-bacterial agent incorporated in the fibers that can inhibit fungal or bacterial growth when the wound dressing is applied to a subject in need thereof.

It will be appreciated that the polymer fibers and/or scaffold can be potentially used in any application where it is desirable to controllably release at least one hydrophobic therapeutic agent or hydrophobic cosmetic agent from the fibers and/or scaffold.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 7:
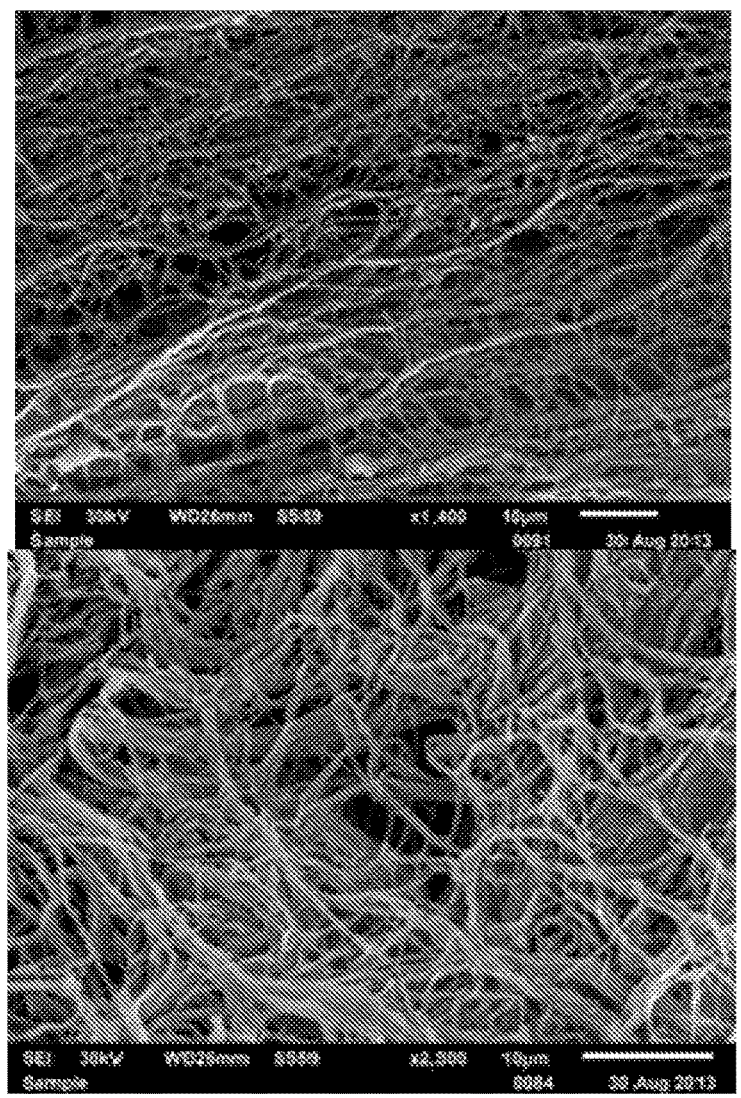
FIG. 7 illustrates SEM images of low and high drug loading fibers (left) 92/8 PCL/clotrimazole co-extruded fibers and (right) 80/20 PCL/clotrimazole co-extruded fibers.

In this example, we used a melt co-extrusion in conjunction with a modular chemistry to yield polyester nanofibers with a hydrophobic drug (clotrimazole). The processing method makes use of the co-extrusion of PEO and PCL with clotrimazole through a series of dye multipliers to form nanofibrous PCL with clotrimazole within a PEO tape. PCL with clotrimazole and PEO are melt-pumped and layered on top of one another in the extrusion line (FIG. 1). From here a vertical multiplier is used to rearrange the extrudate to yield a vertical layer structure (Step A). This is then followed by a series of vertical multipliers that cut the flow horizontally and expands the flow fields in the vertical direction to align in parallel. This process is repeated eight times to yield a vertically aligned, layered flow comprised of alternating PCL with clotrimazole (512 layers) and PEO (512 layers) with 1024 total layers (Step B). The tape is then combined with two surface layers of PEO on the top and bottom (Step C) and is split vertically with one side stacked on top of the other (2x) to yield a PCL nanomatrix embedded in a PEO tape. This procedure is repeated one additional time, and an extrudate containing 512 PCL nanodomains embedded in a PEO matrix is obtained (Step D). The PEO in the tape can be removed by dissolution in a water bath or by using a high pressure water jet to produce a PCL nanofiber matrix including the clotrimazole. A scanning electron micrograph of the PCL fibers after the dissolving procedure shows fibers displaying cross-sectional dimensions of approximately 400-1000 nm by 2-5 μm (FIG. 7). After removal of the PEO matrix, <1% of PEO remained as determined by NMR and DSC (Supporting Information), yielding a scalable PCL nanofiber mat.

Figure 8:
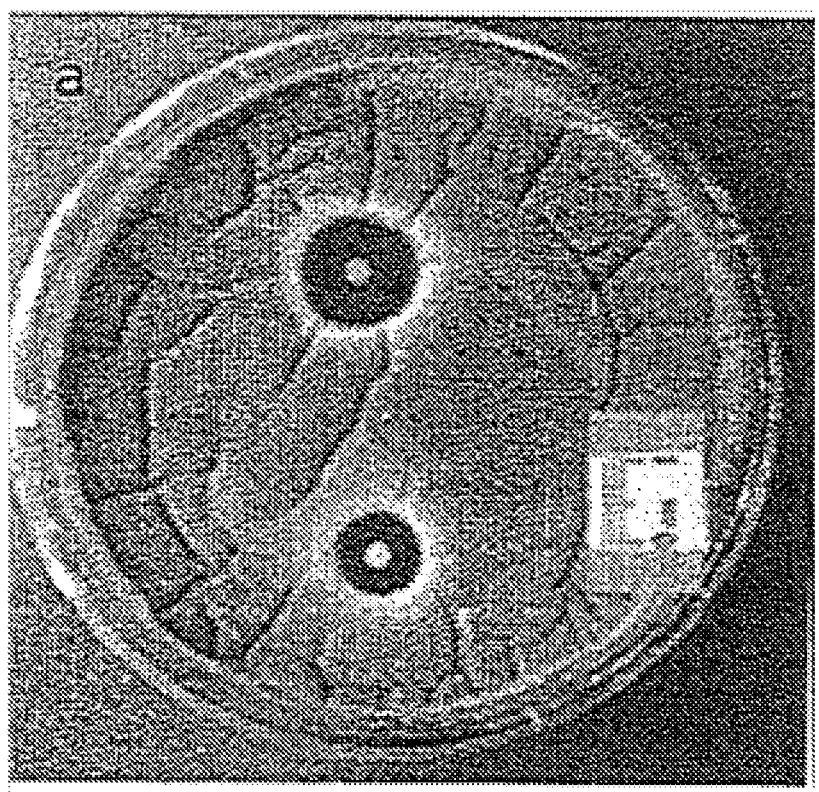
FIG. 8 illustrates an image showing the capacity of co-extruded polymer fiber scaffolds shown in FIG. 7 to clear of *A. fumigatus* and form a zone of inhibition.

The morphology of the produced fibers with two different drug loadings is presented in FIG. 8. It is important to note that the PCL nanofibers have large surface area to volume ratio due to their nanoscale cross sectional dimensions and their rectangular shape, which are advantages for drug delivery applications. It is important to note that this process produces much larger pore size compared to mats created using the electrospun technique.

Figure 9:
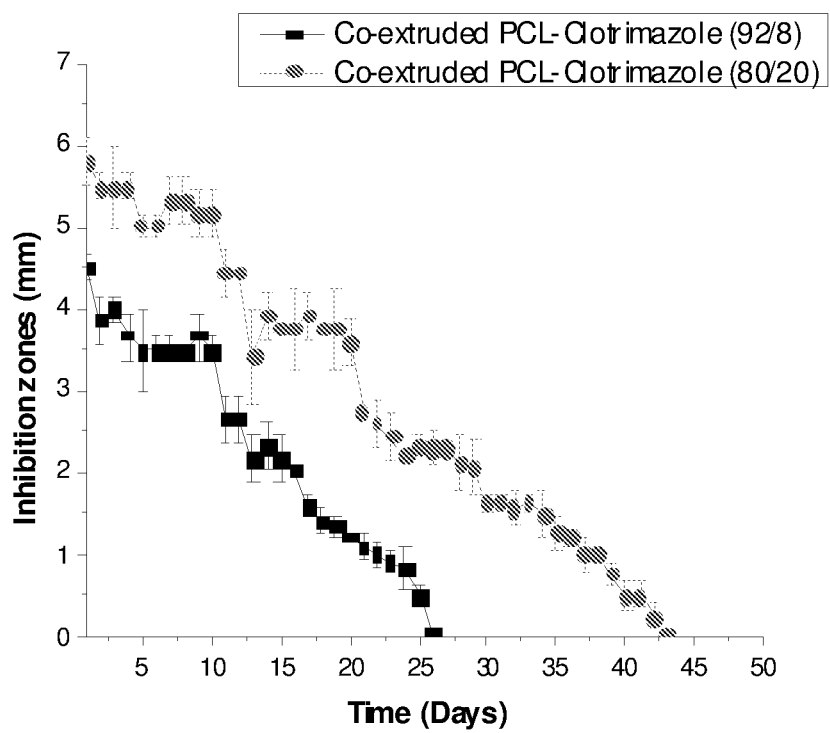
FIG. 9 illustrates plots showing cleared zone size versus number of days cleared for different drug concentration in co-extruded polymer fiber scaffolds of FIG. 7.

The in vitro antifungal properties of the polymer fiber scaffolds containing clotrimazole shown in FIG. 8 were evaluated by the zone of inhibition method against *Aspergillus fumagitus* (FIG. 9). Briefly, *Aspergillus fumagitus* was spread onto agar. Scaffolds were on top of the fungus coated agar and incubated for 37° C. for approximately 24 hours. The zone of inhibition was then measured.

FIG. 9 shows the capacity of a polymer fiber scaffold containing clotrimazole to clear of A fumigatus and form a zone of inhibition.

EXAMPLE 2

Experimental
Materials

Poly(caprolactone) (Capa 6800; number-average molecular weight of 80,000 g/mol) with a reported melt flow index (MFI) of 3 g/(10 min) was supplied from Perstorp. Poly (ethylene oxide) (PolyOx WSR N-10, $M_W$=100,000 g/mol; and PolyOx WSR N-80, $M_W$=200,000 g/mol)) were obtained from the Dow Chemical Company. Both PCL and PEO were dried in a vacuum of −30 inHg for 48 h at 45° C. to remove the moisture prior to processing. Clotrimazole was obtained from Sigma-Aldrich. The same PCL (molecular weight $M_n$=80,000 g/mol) was used in electrospinning and co-extrusion processes. Chloroform and methanol were stored and used as received.

Co-Extrusion

A solid dispersion of the clotrimazole in PCL was prepared at two different weight percentages, namely 6.10 wt % and 10.35 wt %. Two PEO powders of different molecular weights (100 kD and 200 kD) were melt-blended at 140° C. in a co-rotating twin-screw extruder (Thermo Scientific TSE 24 MC) with a screw length/diameter ratio of 40:1 after drying under vacuum of −30 inHg at 40 ° C. for 48 h. The blend was a 30:70 (by weight) mixture of N80:N10 to create a rheological viscosity match with PCL during microlayer co-extrusion. Melt viscosities were obtained on a Galaxy I Model D7054 melt flow indexer (Kayeness Inc.) at a shear rate of $10s^{-1}$ to simulate extrusion conditions. A temperature of 180° C. was chosen based on a viscosity match ($\eta_{PCL:Clotrimazole}$≈0.057 MPa·s; $\eta_{PEO}$≈0.053 MPa·s) for multilayer co-extrusion to mitigate any degradation of clotrimazole during the ca. 25-minute residence time of the extruder. Prior to co-extrusion, all materials were again dried under vacuum of −30 inHg at 40° C. for 48 h to remove moisture. A multilayered polymer composite film with alternating PCL nanofibers embedded in a PEO tape was produced by using the vertical multiplication technique as described previously. The temperature of the extruder, multiplying elements, multiplying die and exit die were set to 180° C. to match the viscosities of the polymer melts as closely as possible. As a result of the co-extrusion process, the multilayered composite tapes with 4096 rectangular PCL fiber domains embedded in PEO matrix were co-extruded with the feed ratio to the extruders as (PCL/PEO) (wt %/wt %) 50/50. The sacrificial PEO component was removed through immersion in distilled water for 7 days followed by drip-drying for 24 h and the wash was collected followed by evaporation of water and drying after which the PEO was weighed. Typically, 95-98% of total PEO can be removed in this manner Electrospinning PCL ($M_n$=80,000 g/mol) was dissolved in 3:1 chloroform: methanol to prepare 10 wt % solutions containing two different weight ratios of PCL to clotrimazole, namely 96:4 and 92:8. Optimal electro spinning conditions were a flow rate of 0.8 mL/hr and an applied voltage of 15-20 kV with a needle to rotating collector gap of 12 cm.

In-Vitro Antifungal Activity Studies

The in-vitro antifungal activity of clotrimazole in electrospun and co-extruded nanofibers was determined against *A. fumigatus, C. albican,* and *T mentagrophytes* using a zone of inhibition assay (strains were obtained from the culture collection at the Center for Medical Mycology). Fungal strains used in this study were cultured on plates of Potato Dextrose Agar (PDA, Difco Laboratories, Detroit, Mich.)). Several Petri dishes were plated with fungi on PDA and incubated at 37° C. for 3-5 days. At the end of the incubation period, conidia were scraped from the plates with sterile cell scrapers (BD Falcon; BD Biosciences, Bedford, Mass.) in normal sterile saline (0.85% NaCl). A challenge inoculum of $10^7$ conidia/10 μl was prepared using a hemacytometer. All media preparations were done according to the manufacturer's instructions. Clotrimazole-containing PCL fiber mats were placed on seeded plates and then incubated for up 48 h at 37° C., and the zone of inhibitions was measured. The same preparation method was used for in-vivo test to evaluate the antifungal activity of the scaffolds infused with clotrimazole.

Animal Inoculation and PCL-Clotrimazole Treatment

Challenge inoculum ($10^7$ conidia/10 µl) was prepared as described above. Outbred CD-1 mice (weight range of 30-60 gm), which are more representative of the general human population, were purchased from Charles River, Willmington, Va. and used in this study. All procedures in the protocol were in compliance with the guidelines of the Animal Welfare Act, the Guide for the Care and Use of Laboratory Animals, and the Office of Laboratory Welfare. The protocol for animal infection was approved by the Institutional Animal Care and Use Committee (IACUC) at the Case Western Reserve University School of Medicine, Cleveland. Animals were allowed to acclimate for a minimum of 5 days prior to use. Environmental controls for the animal room were set to maintain a temperature of 16 to 22° C., a relative humidity of 30-70%, and a 12:12 light-dark cycle. All procedures were performed while the animals were under general anesthesia, and all efforts were made to minimize animal suffering. The mice were anesthetized by administering ketamine, and xylazine intraperitoneally. A 3×3 cm² midline back area was delineated, shaved and depilated. The dorsal area was prepared for wounding using a betadine scrub and wiping with 70% alcohol. On one side of the back a stainless steel wire ring (16 mm diameter and 19 gauge) was secured to the skin with wound clips 2-5 mm to the left of midline. After splint placement, 6 mm full thickness excisional wounds were created with a 6 mm sterile disposable punch biopsy (Miltex, Inc., York, Pa.) in the center of each splint. The area was inoculated with 10 µl of 1×$10^7$ of *A. fumigatus*. After infection of the wound, a separate sterile wound dressing (Tegaderm™ Film, 3M Health Care, Neuss Germany) was placed over the infected area. Infected mice were randomized into the following groups (5 per group): Infected treated with (PCL:clotrimazole)/PEO-infused patches PCL:clotrimazole-infused patches, and PCL patch. Patches were applied to the infected area beginning 2 h post challenge and remained in place for 7 days. Patches were replaced as needed. Mice were euthanized one day after the last day of treatment. The infected area was removed aseptically and weighed. Tissue was homogenized and serially diluted in normal saline. Aliquots of the homogenates were spread on the surface of Sabouraud Dextrose agar (SDA, Beckton, Dickinson and Company, Sparks, Md.) plates, incubated for 48 hr at 32° C. Following incubation, colony forming units (CFUs) were determined. Tissue fungal burden was expressed as CFUs/gram of tissue.

Results and Discussion

Scanning Electron Microscopy

The SEM nanofibrous structure of co-extruded and electrospun are shown in FIG. 10. We note that the fibers from the co-extrusion process are rectangular (thickness=2.89±1.23 µm, width=0.98±0.65 µm) rather than cylindrical due to cutting and layering steps. The electrospun fibers have an average diameter between 0.8-1.1 µm. Fiber diameter and pore diameters of coextruded fibers in FIG. 10 can be tuned depending on processing conditions. For example, if desired, smaller-diameter fibers can be produced using higher number of multipliers.

Thermogravimetric Analyses

Figure 11:
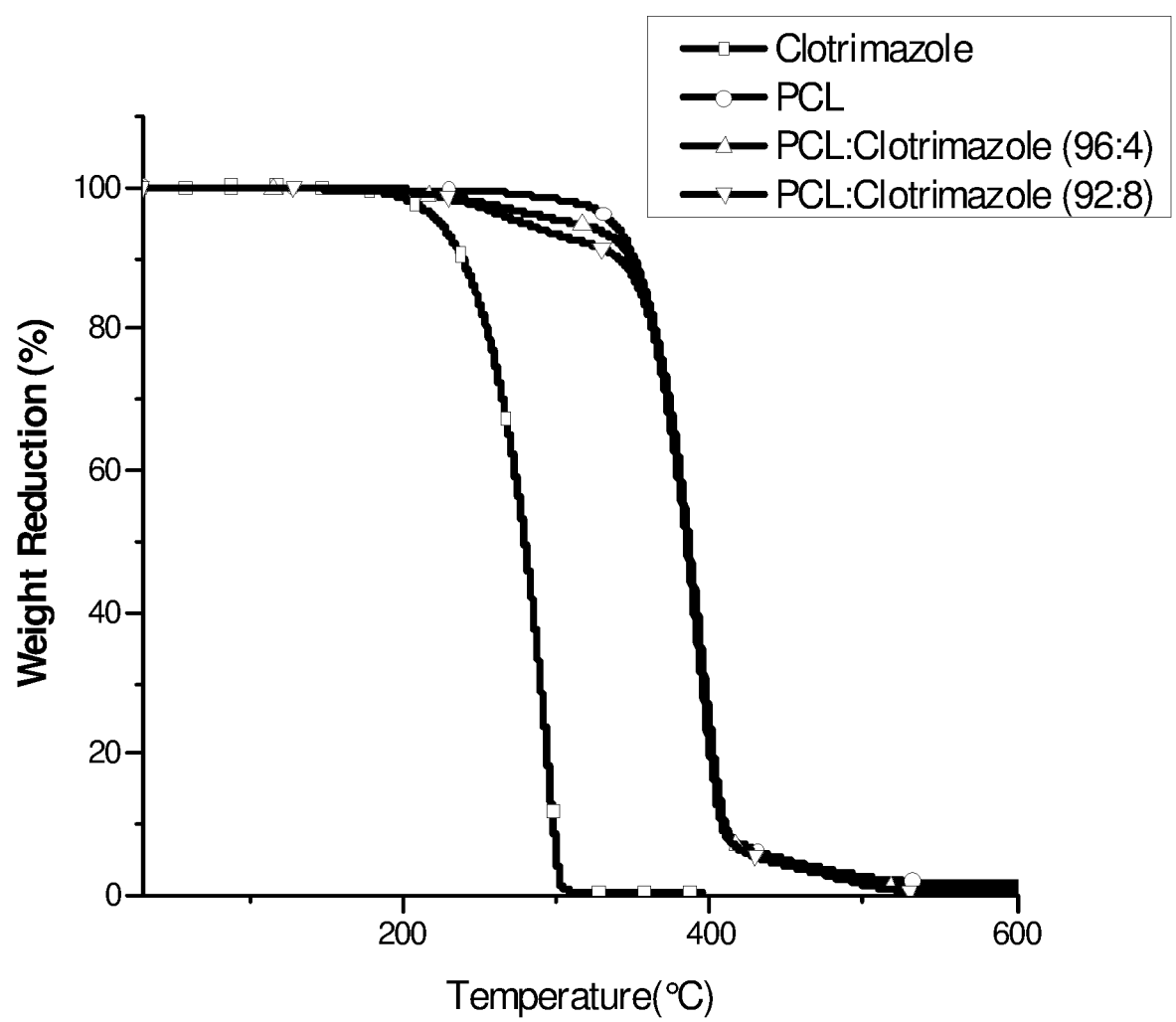
FIG. 11 illustrates TGA scans of PCL, Clotrimazole and PCL:Clotrimazole.

TGA experiments indicate that clotrimazole, PCL, and PCL:Clotrimazole blends are stable at the processing temperature of 180° C. Using the non-isothermal mode, it was observed that clotrimazole alone begins to decompose above 190° C. Upon blending the drug with the polymer, the weight loss of clotrimazole as a function of time was significantly reduced indicated by the TGA scans in FIG. 11.

Differential Scanning calorimetry Analysis (DSC) and X-Ray Diffraction (XRD)

Figure 12:
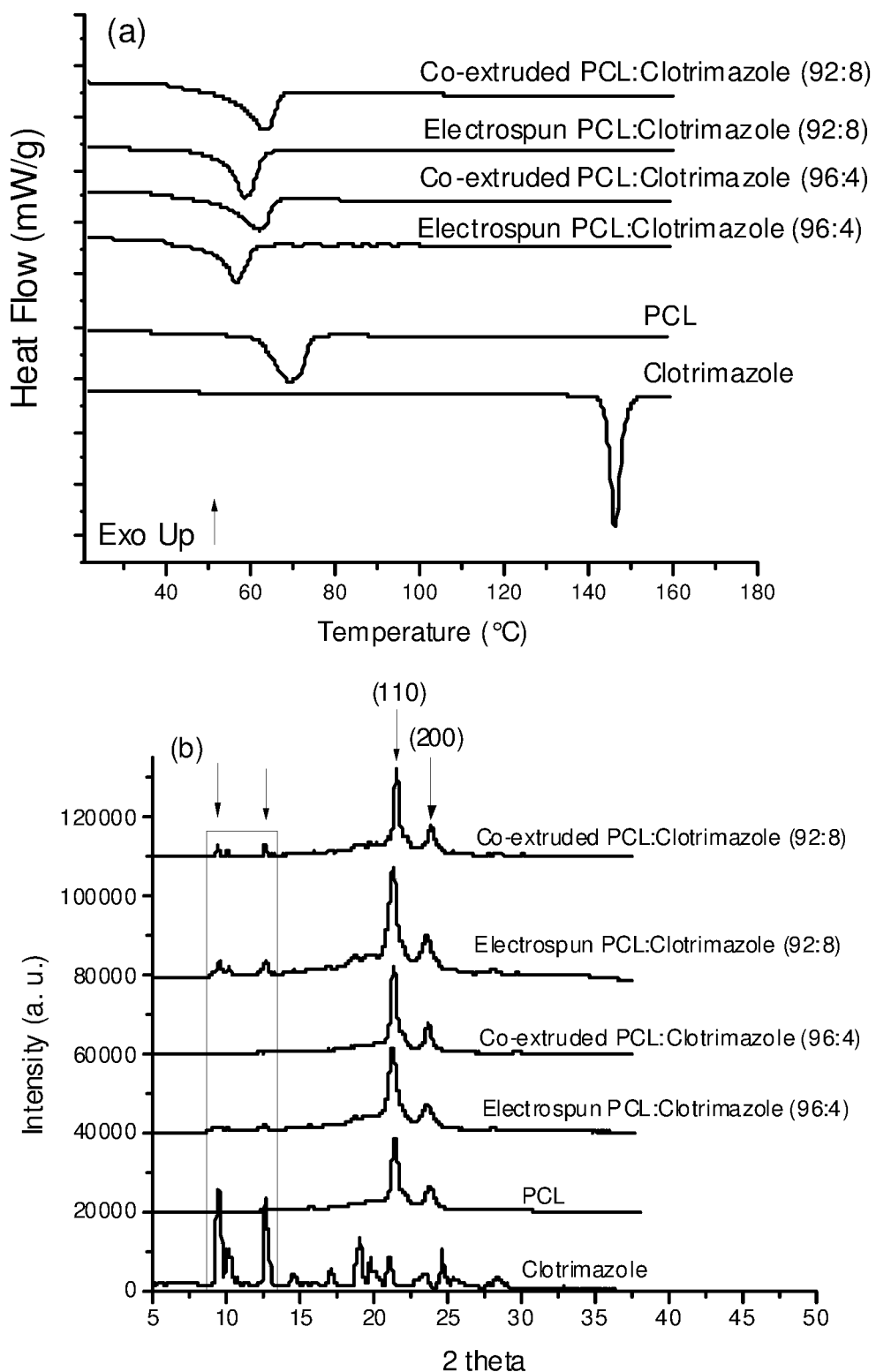
FIGS. 12A-B illustrate (A) DSC and (B) XRD of PCL, Clotrimazole and PCL:Clotrimazole 4%, and 8% electrospun and co-extruded fibers.

FIG. 12 shows overlays of DSC thermograms of clotrimazole, PCL, and the electrospun and co-extruded scaffolds containing 4 and 8 wt % of clotrimazole. The degree of crystallinity of PCL, $X_{PCL}$, was calculated using DSC data and the following relationship:

$$X_{PCL} = \frac{\Delta H_{PCL}}{W_{PCL}\Delta H_{PCL,pure}} \quad (1)$$

where $\Delta H_{PCL}$, $W_{PCL}$, $\Delta H_{PCL,pure}$ are the calculated melting enthalpy of the PCL:clotrimazole scaffold, the PCL weight content in scaffolds and the heat of fusion for PCL crystals, and the enthalpy of fusion ($\Delta H_{PCL,pure}$) is taken to be 139.5 J/g.

It was found that the percent crystallinities of electrospun PCL (44.6%) and as-extruded (45.7%) PCL fibers are very similar. It was also found that the addition of clotrimazole during co-extrusion somewhat increases the % crystallinity of PCL. For example, increasing the drug concentration from 4% to 8 wt % increases the crystallinity from 48.2% to 52.3%. The DSC melting endotherm for PCL in the co-extruded and electrospun fibers is shifted to the lower temperatures, suggesting somewhat smaller average crystallite sizes in PCL co-extruded with the drug, and is especially notable with the electrospun PCL.

X-ray diffraction (XRD) studies were performed on the co-extruded and electrospun scaffolds and pure clotrimazole. Results are shown in FIG. 12. Clotrimazole has primary diffraction peaks at 2θ values of 9.15 and 12.35. Weak reflections apparently corresponding to clotrimazole are observed in both the electrospun and co-extruded PCL containing the higher level (8 wt %) of clotrimazole, suggesting that the solubility limit for the drug in PCL amorphous domains begins to exceed saturation.

Surface Area and Porosity Analysis

The BET technique relies on the surface adsorption of gas molecules; the total mass of the gas adsorbed allows one to calculate the area of the surface. Our BET measurements indicate that co-extruded nanofibers have about a three times higher surface area in comparison to our electrospun fibers (FIG. 13). SEM images shown earlier confirm that a larger pore size of co-extruded vs. electrospun fibers. The small fiber dimensions, the high specific surface area and larger pore sizes of co-extruded polymer can afford an increased dissolution rate of clotrimazole.

Elemental Analysis

Chlorine analysis was conducted on two different PCL-clotrimazole compositions (extruder feed compositions (6.10 wt % and 10.35 wt %) after extrusion and PEO extraction to isolate fiber mats. The respective clotrimazole amounts found were 3.87% and 7.87% respectively, indicating of loss of about 37% for the initial 6.10 wt % sample, and about 24% for the 10.35 wt % sample. The loss is likely the result of some clotrimazole partitioning into the PEO phase during processing which is lost on water washing, with perhaps some clotrimazole being extracted during the PEO dissolution step over several days. The clotrimazole compositions for the electrospun samples (4 wt % and 8 wt %) were chosen to match those of the co-extruded samples after extraction. Chlorine analysis of the electrospun samples indicated a clotrimazole composition of 3.92 and 8.12 wt %, indicating that the amount of drug in the electrospun fibers closely matched that of the feed.

In-Vitro and In-Vivo Antifungal Activities

Figure 14:
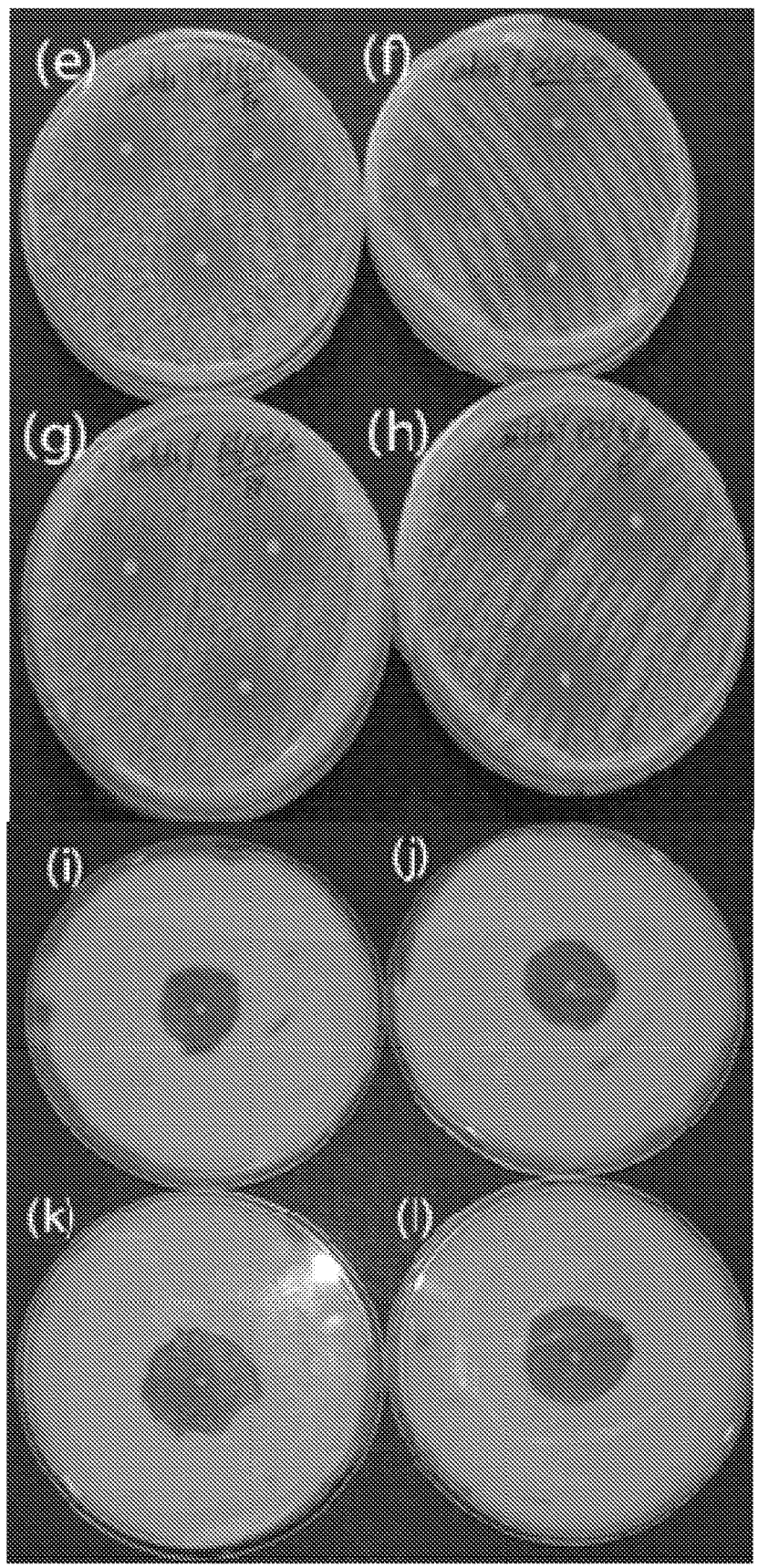
FIGS. 14(A-L) illustrate zones of inhibition of PCL: Clotrimazole from (A) 4 wt % co-extruded against *A. fumigatus,* (B) 4 wt % electrospun fibers *A. fumigatus,* (C) 8 wt % co-extruded against *A. fumigatus,* (D) 8 wt % electrospun fibers against *A. fumigatus,* (E) 4 wt % co-extruded against *C. albicans,* (F) 4 wt % electrospun fibers against *C. albicans,* (G) 8 wt % co-extruded against *C. albicans,* (H) 8 wt % electrospun fibers against *C. albicans,* (I) 4 wt % co-extruded against *T. mentagrophytes,* (J) 4 wt % electrospun fibers *T. mentagrophytes,* (K) 8 wt % co-extruded against *T. mentagrophytes,* (L) 8 wt % electrospun fibers against *T. mentagrophytes.*
Figure 15:
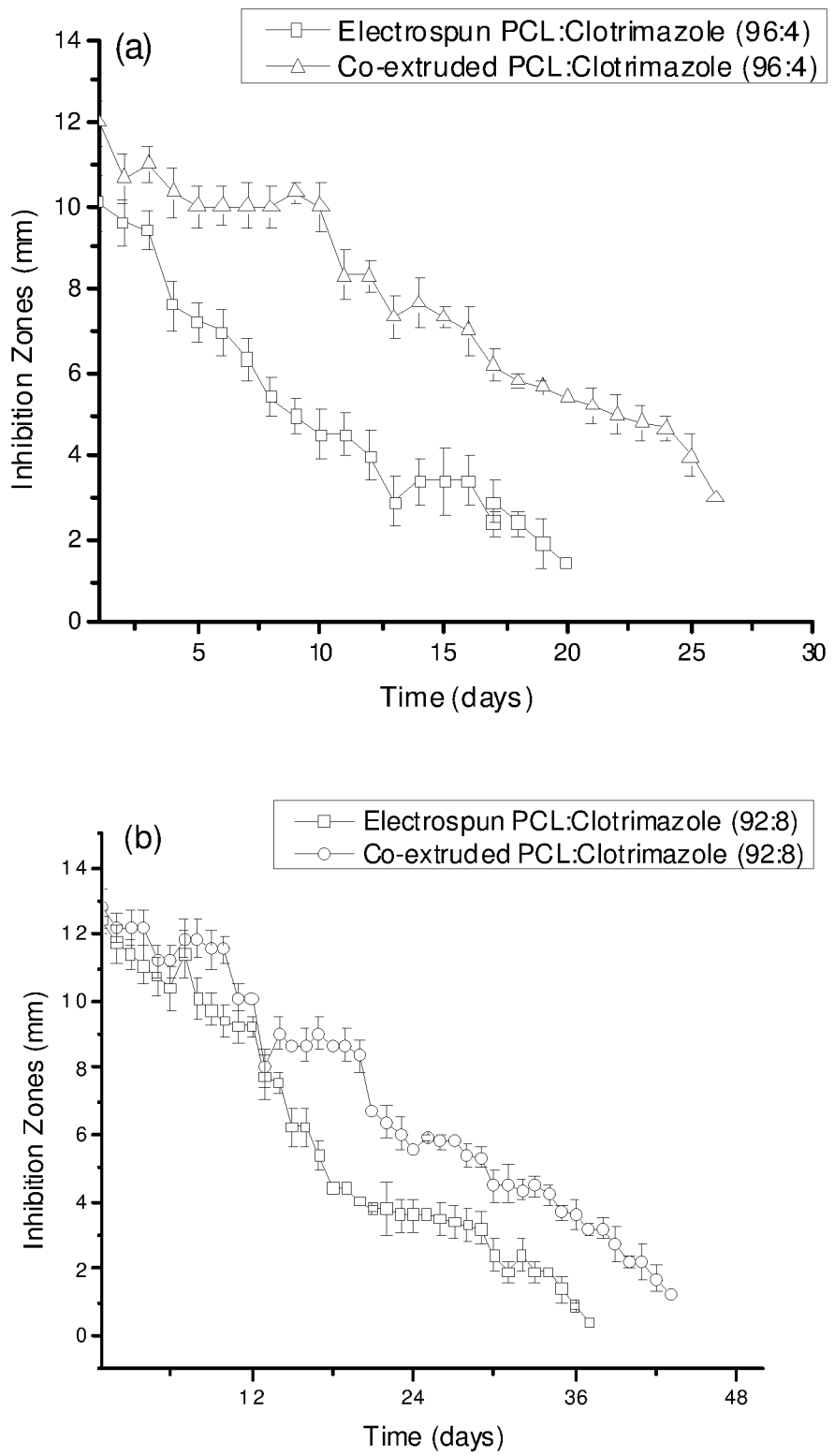
FIGS. 15(A-B) illustrate inhibition zones vs. time for co-extruded and electrosun nanofibers (A) PCL:Clotrimazole 4 wt % (B) PCL:Clotrimazole 8 wt % against *A. fumigatus.*

The performance of antimicrobial disk diffusion susceptibility testing is monitored which zone diameter ranges (in millimeters) of acceptable reproducibility have been established. The zone of inhibitions is shown in FIG. 14 as determined for 4 and 8 wt % of PCL-clotrimazole electrospun and co-extruded fibers. The antifungal activity of electrospun and co-extruded fibers were measured in terms of the diameter of the zone of inhibition (FIG. 15). A comparison of the co-extruded fiber mats (12 mm) with electrospun samples (11 mm) showed larger inhibition zone of A. fumigatus to clotrimazole in the former. The inhibition zone efficacies of PCL-clotrimazole co-extruded fibers against *C. albican,* and *T mentagrophytes* (0.9 mm, 47 mm) were larger compared to PCL-clotrimazole electrospun (0.8 mm, 40 mm) respectively. This indicates that the co-extruded fibers exhibited quite strong antifungal ability and great potential for applications in the wound dressing field (FIG. 15). We speculate that melt co-extrusion may lead to better molecular dispersion of clotrimazole in PCL compared with electrospinning, where in the latter rapid solvent evaporation during fiber formation can result in more inhomogeneous incorporation of drug in the quickly solidified fibers. Importantly, the co-extruded 8 wt % clotrimazole-containing PCL fibers exhibited activity for more than six weeks, which is attractive for clinical applications.

Figure 16:
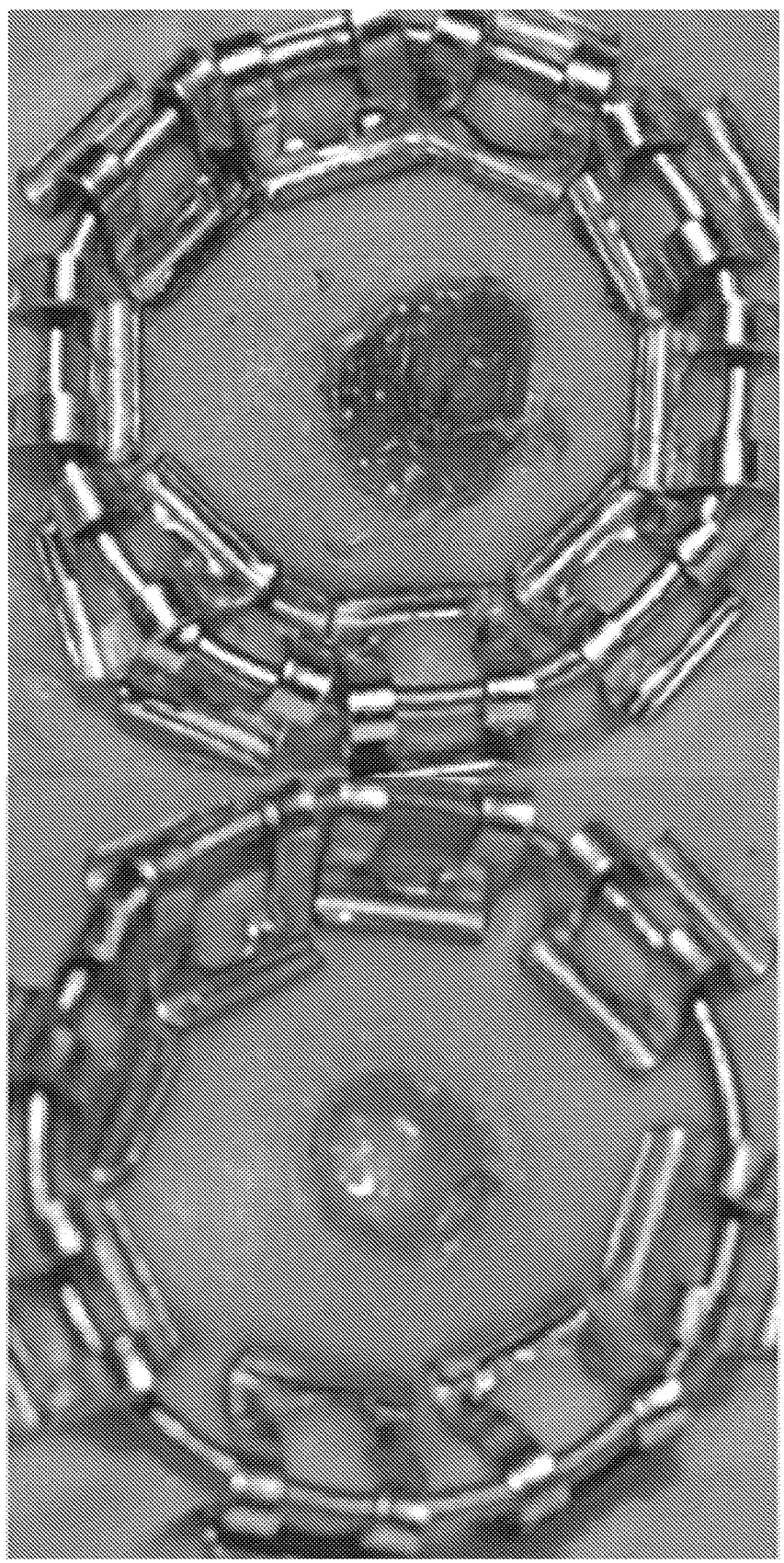
FIGS. 16(A-B) illustrate images of wounds taken 7 days post infection A). Treated with Vehicle PCL Patch, and B). Treated with clotrimazole-infused PCL patch.
Figure 17:
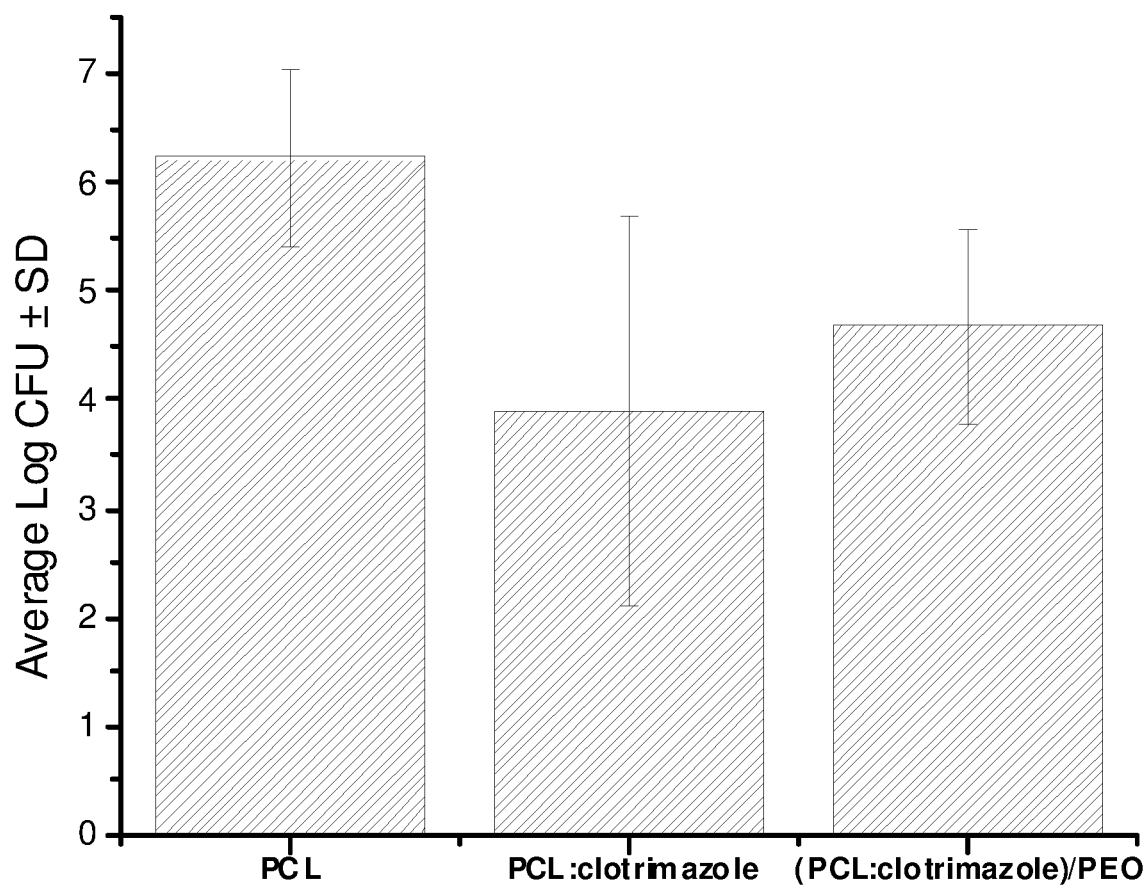
FIG. 17 illustrates tissue fungal burden expressed as average log colony forming unit CFU/g of tissue and standard deviation.

In the in-vivo mouse study, tissue fungal burden was assessed one day after the last treatment. As can be seen in FIG. 16, the fungal burdens were analyzed and given as average log CFUs±the standard deviation. As expected the vehicle control group had the highest average log CFU, 6.23±0.8. The tissue fungal burden for the (PCL-clotrimazole)/PEO treated group was 4.68±0.9. While, treatment with PCL-clotrimazole showed the lowest tissue fungal burden of 3.89±1.7. Importantly, treatment with PCL-clotrimazole resulted in significantly lower microbial burden when compared to the PCL patch and untreated controls (FIG. 17).

A continuous co-extrusion process has been applied successfully to pharmaceutical formulations, specifically demonstrating incorporation of clotrimazole in PCL fibers and subsequent release of active drug. Advantages offered over eletrospinning of clotrimazole-containing PCL fibers include a higher throughput and extended activity in in-vitro experiments. It is believed the latter is due to a more homogeneous incorporation of clotrimazole into PCL by virtue of melt-mixing vs. the rapid evaporation event during solvent-based electrospinning From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A multilayered polymer composite film comprising:
a water-soluble polymer matrix and a plurality of fibers embedded within the water soluble polymer matrix; the fibers including a water insoluble polymer material and at least one of a non-polymeric hydrophobic therapeutic agent or a non-polymeric hydrophobic cosmetic agent homogenously dispersed in the water insoluble polymer material, the fibers having a rectangular cross-section, and each fiber extending the entire length of the multilayered polymer composite film; and the fibers having a surface area to volume ratio of at least about 4 $m^2/g$.

2. The multilayer polymer composite film of claim 1, wherein the hydrophobic therapeutic agent is at least partially soluble in the water insoluble polymer material.

3. The multilayer composite film of claim 1, wherein the water soluble polymer is coextruded with the water insoluble polymer material and the at least one of a non-polymeric hydrophobic therapeutic agent or a non-polymeric hydrophobic cosmetic agent.

4. The multilayer composite film of claim 3, wherein the water insoluble polymer material is substantially immiscible with the water soluble polymer during coextrusion.

5. The multilayer composite film of claim 1, wherein the water soluble polymeric matrix comprises polyethylene oxide and the water insoluble polymer material comprises polycaprolactone.

6. The multilayer composite film of claim 1, wherein the non- polymeric hydrophobic therapeutic agent is clotrimazole.

7. The multilayer composite film of claim 1, wherein the fibers comprise about 1% to about 50% by weight of the non-polymeric hydrophobic therapeutic agent or a non-polymeric hydrophobic cosmetic agent.

8. A polymer nanofiber scaffold comprising:
a plurality of melt extruded polymer nanofibers, the nanofibers each having a rectangular cross-section defined in part by an encapsulating polymer material that is separated from the nanofibers, the nanofibers including a water insoluble polymer material and at least one of a non-polymeric hydrophobic therapeutic agent or a non-polymeric hydrophobic cosmetic agent homogenously dispersed in the water insoluble polymer material.

9. The scaffold of claim 8, wherein the hydrophobic therapeutic agent is at least partially soluble in the water insoluble polymer material.

10. The scaffold of claim 8, wherein the fibers having a surface area to volume ratio of at least about 4 $m^2/g$.

11. The scaffold of claim 8, wherein a water soluble polymer is coextruded with the water insoluble polymer material and the at least one of a non-polymeric hydrophobic therapeutic agent or a non-polymeric hydrophobic cosmetic agent.

12. The scaffold of claim 11, wherein the water insoluble polymer material is substantially immiscible with the water soluble polymer during coextrusion.

13. The scaffold of claim 8, wherein the water insoluble polymer comprises polycaprolactone.

14. The multilayer composite film of claim 8, wherein the non- polymeric hydrophobic therapeutic agent is clotrimazole.

15. The scaffold of claim 8, wherein the fibers comprise about 1% to about 50% by weight of the non-polymeric hydrophobic therapeutic agent or a non-polymeric hydrophobic cosmetic agent.

16. A polymer nanofiber scaffold comprising:
a plurality of melt extruded polymer nanofibers, the nanofibers each having a rectangular cross-section defined in part by an encapsulating polymer material that is separated from the nanofibers, the nanofibers including a water insoluble polymer material and clotrimazole homogenously dispersed in the water insoluble polymer matrix of the water insoluble polymer material;
wherein the fibers having a surface area to volume ratio of at least about 4 $m^2/g$.

17. The scaffold of claim 16, wherein the water insoluble polymer material comprises polycaprolactone.

\* \* \* \* \*